(12) United States Patent
Svetlichny et al.

(10) Patent No.: US 12,359,229 B2
(45) Date of Patent: *Jul. 15, 2025

(54) **EXTREME THERMOPHILIC BACTERIA OF THE GENUS *CALDICELLULOSIRUPTOR* SUITABLE FOR THE CONVERSION OF CELLULOSIC AND STARCHY BIOMASS**

(71) Applicant: BLUCON BIOTECH GMBH, Cologne (DE)

(72) Inventors: Vitaly Svetlichny, Cologne (DE); Marco Krämer, Pullheim (DE); Tatiana Svetlichnaya, Cologne (DE)

(73) Assignee: BLUCON BIOTECH GMBH, Cologne (DE)

( * ) Notice: Subject to any disclaimer, the term of this patent is extended or adjusted under 35 U.S.C. 154(b) by 707 days.

This patent is subject to a terminal disclaimer.

(21) Appl. No.: 17/604,630

(22) PCT Filed: Apr. 20, 2020

(86) PCT No.: PCT/EP2020/060966
§ 371 (c)(1),
(2) Date: Oct. 18, 2021

(87) PCT Pub. No.: WO2020/212620
PCT Pub. Date: Oct. 22, 2020

(65) Prior Publication Data
US 2022/0267814 A1     Aug. 25, 2022

(30) Foreign Application Priority Data

Apr. 18, 2019  (WO) ................ PCT/EP2019/060092
Jan. 10, 2020  (WO) ................ PCT/EP2020/050508

(51) Int. Cl.
*C12P 7/56*     (2006.01)
*C12N 1/20*     (2006.01)
(Continued)

(52) U.S. Cl.
CPC ................ *C12P 7/56* (2013.01); *C12N 1/205* (2021.05); *C12N 1/22* (2013.01); *C12P 2203/00* (2013.01); *C12R 2001/145* (2021.05)

(58) Field of Classification Search
CPC ........ C12P 7/56; C12P 2203/00; C12N 1/205; C12N 1/22; C12R 2001/145
See application file for complete search history.

(56) References Cited

U.S. PATENT DOCUMENTS

2014/0120592 A1    5/2014  Cha et al.

FOREIGN PATENT DOCUMENTS

RU      2671528 C2      1/2018
WO   2013041667 A2      3/2013
(Continued)

OTHER PUBLICATIONS

Rainey et al. "Description of *Caldicellulosiruptor saccharolyticus* gen. nov., sp. nov: An obligately anaerobic, extremely thermophilic, cellulolytic bacterium," FEMS Microbiology Letters, 1994, 120:263-266.

(Continued)

*Primary Examiner* — Louise W Humphrey
*Assistant Examiner* — Rachel Emily Martin
(74) *Attorney, Agent, or Firm* — Raymond Wagenknecht Biotech Beach Law PC

(57) ABSTRACT

Isolated cellulolytic extreme thermophilic bacterial cells belonging to the genus *Caldicellulosiruptor*, mutants thereof, isolated strains, microbial cultures and microbial compositions. The novel bacteria are in particular suitable for the production of fermentation products such as lactic acid from any carbon source, not limited to cellulosic material but especially useful for converting cellulosic bio- (Continued)

16SrDNA consensus sequence for *Caldicellulosiruptor spec.* BluCon006 (SEQ ID NO. 1)

```
   1 GCATGCAGTC GAGCGGAGAT GGTGGTTGAA GGTGATGAGC TGGAGGCTGC CATCTTAGCG
  61 GCGGACGGGT GAGTAACACG TGAGCAACCT ACCCCCAGCA CGGGGATAAC AGCTCGAAAG
 121 GGCTGCTAAT ACCCGATGGG ACCACGTCAT CGCATGGTGA TGTGGTGAAA GGGCTGGGGA
 181 TGGGCTCGCG GCCCATCAGC TAGTTGGTGN GGTAACGGCN NACCAAGGCG ACGACGGGTA
 241 GCCGGGCCTGA GAGGGTGTAC GGCCACAGTG GGACTGAGAC ACGGCCCACA CTCCTACGGG
 301 AGGCAGCAGC GGGGAATCTT GCGCAATGGG CGGAAGCCTG ACGCAGCGAC GCCGCGTGAG
 361 GGAAGAAGCC CTTCGGGGTG TAAACCTCTT TGGACGGGGA GAAGTAGGAG ATAGTACCCG
 421 TTTAAAAAGC CACGGCTAAC TACGTGCCAG CAGCCGCGGT AATACGTAGG TGGCGAGCGT
 481 TGTCCGGAAT TACTGGGCGT AAAGGGTGCG TAGGCGGCTA TGCGAGTTAA GCGTGAAAGC
 541 CTTAGGCTCA ACCTAAGGAT TGCGCTTAAT ACTGCATAGC TTGAGTGCGG GAGAGGACGG
 601 CGGAATTCCC GGTGTAGCGG TGAAATGCGT AGATATCGGG AGGAACACCA GTGGCGAAGG
 661 CGGCCGTCTG GACCGTAACT GACGCTGAGG CACGAAAGCG TGGGGAGCGA ACAGGATTAG
 721 ATACCCTGGT AGTCCACGCT GTAAACGATG GATGCTAGGT GTGGGGGAGA AGGACTCNTC
 781 CGTGCCGTAG TTAACACAAT AAGCATCCCG CCTGGGGAGT ACGGCCGCAA GGTTGAAACT
 841 CAAAGGAATT GACGGGGGCC CGCACAAGCG GTGGAGCATG TGGTTTAATT CGAAGCAACG
 901 CGAAGAACCT TACCAGGGCT TGACATGCCG GGGACCTGCC CGAAAGGGTG GGGTGCCTGT
 961 TCGATGAGAG CAGGAGCCCG GACACAGGTG GTGCATGGTT GTCGTCAGCT CGTGTCGTGA
1021 GATGTTGGGT TAAGTCCCGC AACGAGCGCA ACCCCTGCCC TTAGTTGCCA GCGCGTAATG
1081 GTGGGCACTC TAAGGGGACT GCCGTCGATG AGGCGGAGGA AGGTGGGGAT GACGTCAAAT
1141 CATCATGCCC CTTATGCCCT GGGCTACACA CGTGCTACAA TGGGTGCTAC AGAGGGCGTG
1201 CGAAGGCGCG AGCGGAGCG AATCCCAAAA AAGCACCCCC AGTTCGGATT GCAGGCTGCA
1261 ACTCGCCTGC ATGAAGTCGG AATCGCTAGT AATCGCGGAT CAGCATGCCG CGGTGAATAC
1321 GTTCCCGGGC CTTGTACACA CCGCCCGTCA CACCATGAGA GTCAGCAACA CCTGAAGACA
1381 CAGGTTAAGC TGTGTTGAAG GTGGGGCTGA TGATTGGGGT GAAGTCGTAA CAAGGTAGCC
1441 GTACGGGAAC GTGCGGCTG
``` mass like ligniocellulosic biomass and/or starch containing biomass.

19 Claims, 10 Drawing Sheets

Specification includes a Sequence Listing.

(51) Int. Cl.
*C12N 1/22* (2006.01)
*C12R 1/145* (2006.01)

(56) References Cited

FOREIGN PATENT DOCUMENTS

| WO | 2013041669 A1 | 3/2013 | |
|---|---|---|---|
| WO | WO-2014009273 A1 * | 1/2014 | ............... C12N 1/20 |
| WO | 2016016233 A1 | 2/2016 | |

OTHER PUBLICATIONS

PCT/EP2020/060966 International Search Report and Written Opinion dated May 20, 2020.
Office Action for RU 2021131526/10(066855) mailed Aug. 24, 2023.

* cited by examiner

**16SrDNA consensus sequence for *Caldicellulosiruptor spec.* BluCon006 (SEQ ID NO. 1)**

```
   1 GCATGCAGTC GAGCGGAGAT GGTGGTTGAA GGTGATGAGC TGGAGGCTGC CATCTTAGCG
  61 GCGGACGGGT GAGTAACACG TGAGCAACCT ACCCCCAGCA CGGGGATAAC AGCTCGAAAG
 121 GGCTGCTAAT ACCCGATGGG ACCACGTCAT CGCATGGTGA TGTGGTGAAA GGGCTGGGGA
 181 TGGGCTCGCG GCCCATCAGC TAGTTGGTGN GGTAACGGCN NACCAAGGCG ACGACGGGTA
 241 GCCGGCCTGA GAGGGTGTAC GGCCACAGTG GGACTGAGAC ACGGCCCACA CTCCTACGGG
 301 AGGCAGCAGC GGGGAATCTT GCGCAATGGG CGGAAGCCTG ACGCAGCGAC GCCGCGTGAG
 361 GGAAGAAGCC CTTCGGGGTG TAAACCTCTT TGGACGGGGA GAAGTAGGAG ATAGTACCCG
 421 TTTAAAAAGC CACGGCTAAC TACGTGCCAG CAGCCGCGGT AATACGTAGG TGGCGAGCGT
 481 TGTCCGGAAT TACTGGGCGT AAAGGGTGCG TAGGCGGCTA TGCGAGTTAA GCGTGAAAGC
 541 CTTAGGCTCA ACCTAAGGAT TGCGCTTAAT ACTGCATAGC TTGAGTGCGG GAGAGGACGG
 601 CGGAATTCCC GGTGTAGCGG TGAAATGCGT AGATATCGGG AGGAACACCA GTGGCGAAGG
 661 CGGCCGTCTG GACCGTAACT GACGCTGAGG CACGAAAGCG TGGGGAGCGA ACAGGATTAG
 721 ATACCCTGGT AGTCCACGCT GTAAACGATG GATGCTAGGT GTGGGGGAGA AGGACTCNTC
 781 CGTGCCGTAG TTAACACAAT AAGCATCCCG CCTGGGGAGT ACGGCCGCAA GGTTGAAACT
 841 CAAAGGAATT GACGGGGGCC CGCACAAGCG GTGGAGCATG TGGTTTAATT CGAAGCAACG
 901 CGAAGAACCT TACCAGGGCT TGACATGCCG GGGACCTGCC CGAAAGGGTG GGGTGCCTGT
 961 TCGATGAGAG CAGGAGCCCG GACACAGGTG GTGCATGGTT GTCGTCAGCT CGTGTCGTGA
1021 GATGTTGGGT TAAGTCCCGC AACGAGCGCA ACCCCTGCCC TTAGTTGCCA GCGCGTAATG
1081 GTGGGCACTC TAAGGGGACT GCCGTCGATG AGGCGGAGGA AGGTGGGGAT GACGTCAAAT
1141 CATCATGCCC CTTATGCCCT GGGCTACACA CGTGCTACAA TGGGTGCTAC AGAGGGCGTG
1201 CGAAGGCGCG AGCCGGAGCG AATCCCAAAA AAGCACCCCC AGTTCGGATT GCAGGCTGCA
1261 ACTCGCCTGC ATGAAGTCGG AATCGCTAGT AATCGCGGAT CAGCATGCCG CGGTGAATAC
1321 GTTCCCGGGC CTTGTACACA CCGCCCGTCA CACCATGAGA GTCAGCAACA CCTGAAGACA
1381 CAGGTTAAGC TGTGTTGAAG GTGGGGCTGA TGATTGGGGT GAAGTCGTAA CAAGGTAGCC
1441 GTACGGGAAC GTGCGGCTG
```

FIG. 1

**16SrDNA consensus sequence for *Caldicellulosiruptor* sp. BluCon014 (SEQ ID NO. 2)**

```
   1 ACGCATGCAG TCGAGCGGAG ATGGTGGTTG AAGGTGATGA GCTGGAGGCT GCCATCTTAG
  61 CGGCGGACGG GTGAGTAACA CGTGAGCAAC CTACCCCCAG CACGGGGATA ACAGCTCGAA
 121 AGGGCTGCTA ATACCCGATG GGACCACGTC ATCGCATGGT GATGTGGTGA AAGGGCTGGG
 181 GATGGGCTCG CGGCCCATCA GCTAGTTGGT GNGGTAACGG CNNACCAAGG CGACGACGGG
 241 TAGCCGGCCT GAGAGGGTGT ACGGCCACAG TGGGACTGAG ACACGGCCCA CACTCCTACG
 301 GGAGGCAGCA GCGGGGAATC TTGCGCAATG GGCGGAAGCC TGACGCAGCG ACGCCGCGTG
 361 AGGGAAGAAG CCCTTCGGGG TGTAAACCTC TTTGGACGGG GAGAAGTAGG AGATAGTACC
 421 CGTTTAAAAA GCCACGGCTA ACTACGTGCC AGCAGCCGCG GTAATACGTA GGTGGCGAGC
 481 GTTGTCCGGA ATTACTGGGC GTAAAGGGTG CGTAGGCGGC TATGCGAGTT AAGCGTGAAA
 541 GCCTTAGGCT CAACCTAAGG ATTGCGCTTA ATACTGCATA GCTTGAGTGC GGGAGAGGAC
 601 GGCGGAATTC CCGGTGTAGC GGTGAAATGC GTAGATATCG GGAGGAACAC CAGTGGCGAA
 661 GGCGGCCGTC TGGACCGTAA CTGACGCTGA GGCACGAAAG CGTGGGGAGC GAACAGGATT
 721 AGATACCCTG GTAGTCCACG CTGTAAACGA TGGATGCTAG GTGTGGGGGA GAAGGACTCN
 781 TCCGTGCCGT AGTTAACACA ATAAGCATCC CGCCTGGGGA GTACGGCCGC AAGGTTGAAA
 841 CTCAAAGGAA TTGACGGGGG CCCGCACAAG CGGTGGAGCA TGTGGTTTAA TTCGAAGCAA
 901 CGCGAAGAAC CTTACCAGGG CTTGACATGC CGGGGACCTG CCCGAAAGGG TGGGGTGCCT
 961 GTTCGATGAG AGCAGGAGCC CGGACACAGG TGGTGCATGG TTGTCGTCAG CTCGTGTCGT
1021 GAGATGTTGG GTTAAGTCCC GCAACGAGCG CAACCCCTGC CCTTAGTTGC CAGCGCGTAA
1081 TGGTGGGCAC TCTAAGGGGA CTGCCGTCGA TGAGGCGGAG GAAGGTGGGG ATGACGTCAA
1141 ATCATCATGC CCCTTATGCC CTGGGCTACA CACGTGCTAC AATGGGTGCT ACAGAGGGCG
1201 TGCAAGGCG CGAGCCGGAG CGAATCCCAA AAAAGCACCC CCAGTTCGGA TTGCAGGCTG
1261 CAACTCGCCT GCATGAAGTC GGAATCGCTA GTAATCGCGG ATCAGCATGC CGCGGTGAAT
1321 ACGTTCCCGG GCCTTGTACA CACCGCCCGT CACACCATGA GAGTCAGCAA CACCTGAAGA
1381 CACAGGTTAA GCTGTGTTGA AGGTGGGGCT GATGATTGGG GTGAAGTCGT AACAAGGTAG
1441 CCGTACGGGA ACGTGCGGCT
```

FIG. 2

**16SrDNA consensus sequence for *Caldicellulosiruptor* sp. BluCon016 (SEQ ID NO. 3)**

```
   1 CGCATGCAGT CGAGCGGAGA TGGTGGTTGA AGGTGATGAG CTGGAGGCTG CCATCTTAGC
  61 GGCGGACGGG TGAGTAACAC GTGAGCAACC TACCCCCAGC ACGGGGATAA CAGCTCGAAA
 121 GGGCTGCTAA TACCCGATGG GACCACGTCA TCGCATGGTG ATGTGGTGAA AGGGCTGGGG
 181 ATGGGCTCGC GGCCCATCAG CTAGTTGGTG NGGTAACGGC NNACCAAGGC GACGACGGGT
 241 AGCCGGCCTG AGAGGGTGTA CGGCCACAGT GGGACTGAGA CACGGCCCAC ACTCCTACGG
 301 GAGGCAGCAG CGGGGAATCT TGCGCAATGG GCGGAAGCCT GACGCAGCGA CGCCGCGTGA
 361 GGGAAGAAGC CCTTCGGGGT GTAAACCTCT TTGGACGGGG AGAAGTAGGA GATAGTACCC
 421 GTTTAAAAAG CCACGGCTAA CTACGTGCCA GCAGCCGCGG TAATACGTAG GTGGCGAGCG
 481 TTGTCCGGAA TTACTGGGCG TAAAGGGTGC GTAGGCGGCT ATGCGAGTTA AGCGTGAAAG
 541 CCTTAGGCTC AACCTAAGGA TTGCGCTTAA TACTGCATAG CTTGAGTGCG GGAGAGGACG
 601 GCGGAATTCC CGGTGTAGCG GTGAAATGCG TAGATATCGG GAGGAACACC AGTGGCGAAG
 661 GCGGCCGTCT GGACCGTAAC TGACGCTGAG GCACGAAAGC GTGGGAGCG AACAGGATTA
 721 GATACCCTGG TAGTCCACGC TGTAAACGAT GGATGCTAGG TGTGGGGAG AAGGACTCNT
 781 CCGTGCCGTA GTTAACACAA TAAGCATCCC GCCTGGGGAG TACGGCCGCA AGGTTGAAAC
 841 TCAAAGGAAT TGACGGGGGC CCGCACAAGC GGTGGAGCAT GTGGTTTAAT TCGAAGCAAC
 901 GCGAAGAACC TTACCAGGGC TTGACATGCC GGGGACCTGC CCGAAAGGGT GGGGTGCCTG
 961 TTCGATGAGA GCAGGAGCCC GGACACAGGT GGTGCATGGT TGTCGTCAGC TCGTGTCGTG
1021 AGATGTTGGG TTAAGTCCCG CAACGAGCGC AACCCCTGCC CTTAGTTGCC AGCGCGTAAT
1081 GGTGGGCACT CTAAGGGGAC TGCCGTCGAT GAGGCGGAGG AAGGTGGGGA TGACGTCAAA
1141 TCATCATGCC CCTTATGCCC TGGGCTACAC ACGTGCTACA ATGGGTGCTA CAGAGGGCGT
1201 GCGAAGGCGC GAGCCGGAGC GAATCCCAAA AAAGCACCCC CAGTTCGGAT TGCAGGCTGC
1261 AACTCGCCTG CATGAAGTCG GAATCGCTAG TAATCGCGGA TCAGCATGCC GCGGTGAATA
1321 CGTTCCCGGG CCTTGTACAC ACCGCCCGTC ACACCATGAG AGTCAGCAAC ACCTGAAGAC
1381 ACAGGTTAAG CTGTGTTGAA GGTGGGCTG ATGATTGGGG TGAAGTCGTA ACAAGGTAGC
1441 CGTACGGGAA CGTGCGGCT
```

FIG. 3

**16SrDNA consensus sequence for *Caldicellulosiruptor* sp. DIB104C (SEQ ID NO. 4)**

```
   1 GCATGCAGTC GAGCGGAGAT GGTGGTTGAA GGTGATGAGC TGGAGGCTGC CATCTTAGCG
  61 GCGGACGGGT GAGTAACACG TGAGCAACCT ACCCCCAGCA CGGGGATAAC AGCTCGAAAG
 121 GGCTGCTAAT ACCCGATGGG ACCACGTCAT CGCATGGTGA TGTGGTGAAA GGGCTGGGGA
 181 TGGGCTCGCG GCCCATCAGC TAGTTGGTGN GGTAACGGCN NACCAAGGCG ACGACGGGTA
 241 GCCGGCCTGA GAGGGTGTAC GGCCACAGTG GGACTGAGAC ACGGCCCACA CTCCTACGGG
 301 AGGCAGCAGC GGGGAATCTT GCGCAATGGG CGGAAGCCTG ACGCAGCGAC GCCGCGTGAG
 361 GGAAGAAGCC CTTCGGGGTG TAAACCTCTT GGACGGGGA GAAGTAGGAG ATAGTACCCG
 421 TTTAAAAAGC CACGGCTAAC TACGTGCCAG CAGCCGCGGT AATACGTAGG TGCGAGCGT
 481 TGTCCGGAAT TACTGGGCGT AAAGGGTGCG TAGGCGGCTA TGCGAGTTAA GCGTGAAAGC
 541 CTTAGGCTCA ACCTAAGGAT GCGCTTAAT ACTGCATAGC TTGAGTGCGG GAGAGGACGG
 601 CGGAATTCCC GGTGTAGCGG TGAAATGCGT AGATATCGGG AGGAACACCA GTGGCGAAGG
 661 CGGCCGTCTG GACCGTAACT GACGCTGAGG CACGAAAGCG TGGGGAGCGA ACAGGATTAG
 721 ATACCCTGGT AGTCCACGCT GTAAACGATG GATGCTAGGT GTGGGGAGA AGGACTCNTC
 781 CGTGCCGTAG TTAACACAAT AAGCATCCCG CCTGGGGAGT ACGGCCGCAA GGTTGAAACT
 841 CAAAGGAATT GACGGGGGCC CGCACAAGCG GTGGAGCATG TGGTTTAATT CGAAGCAACG
 901 CGAAGAACCT TACCAGGGCT TGACATGCCG GGGACCTGCC CGAAAGGGTG GGGTGCCTGT
 961 TCGATGAGAG CAGGAGCCCG GACACAGGTG GTGCATGGTT GTCGTCAGCT CGTGTCGTGA
1021 GATGTTGGGT TAAGTCCCGC AACGAGCGCA ACCCCTGCCC TTAGTTGCCA GCGCGTAATG
1081 GTGGGCACTC TAAGGGGACT GCCGTCGATG AGGCGGAGGA AGGTGGGGAT GACGTCAAAT
1141 CATCATGCCC CTTATGCCCT GGGCTACACA CGTGCTACAA TGGGTGCTAC AGAGGGCGTG
1201 CGAAGGCGCG AGCCGGAGCG AATCCCAAAA AAGCACCCCC AGTTCGGATT GCAGGCTGCA
1261 ACTCGCCTGC ATGAAGTCGG AATCGCTAGT AATCGCGGAT CAGCATGCCG CGGTGAATAC
1321 GTTCCCGGGC CTTGTACACA CCGCCCGTCA CACCATGAGA GTCAGCAACA CCTGAAGACA
1381 CAGGTTAAGC TGTGTTGAAG GTGGGCTGA TGATTGGGGT GAAGTCGTAA CAAGGTAGCC
1441 GTACGGGAAC GTGCGGCTG
```

FIG. 4

**16SrDNA consensus sequence for *Caldicellulosiruptor* sp. BluCon052 (SEQ ID NO. 5)**

```
cgcatgcaag tcgagcggag atggtggttg aaggtgatga gctggaggct gccatcttag    60
cggcggacgg gtgagtaaca cgtgagcaac ctaccccag cacggggata acagctcgaa   120
agggctgcta atacccgatg ggaccacgtc atcgcatggt gatgtggtga aannnnnnnn   180
ggnngnnnnn nnggctgggg atgggctcgc ggccatcag ctagttggtg nggtaacggc    240
tnaccaaggc gacgacgggt agccggcctg agagggtgta cggccacagt gggactgaga   300
cacggcccac actcctacgg gaggcagcag cggggaatct tgcgcaatgg gcggaagcct   360
gacgcagcga cgccgcgtga gggaagaagc ccttcgggt gtaaacctct ttggacgggg    420
agaagtagga gatagtaccc gtttaaaaag ccacggctaa ctacgtgcca gcagccgcgg   480
taatacgtag gtggcgagcg ttgtccggaa ttactgggcg taaaggtgc gtaggcggct    540
atgcgagtta agcgtgaaag ccttaggctc aacctaagga ttgcgcttaa tactgcatag   600
cttgagtgcg ggagaggacg gcggaattcc cggtgtagcg gtgaaatgcg tagatatcgg   660
gaggaacacc agtggcgaag gcggccgtct ggaccgtaac tgacgctgag gcacgaaagc   720
gtggggagcg aacaggatta gataccctgg tagtccacgc tgtaaacgat ggatgctagg   780
tgtggggag aaggactcnt ccgtgccgta gttaacacaa taagcatccc gcctggggag    840
tacggccgca aggttgaaac tcaaaggaat gacggggggc ccgcacaagc ggtggagcat   900
gtggtttaat tcgaagcaac gcgaagaacc ttaccagggc ttgacatgcc gggacctgc    960
ccgaaagggt ggggtgcctg ttcgatgaga gcaggagccc ggacacaggt ggtgcatggt  1020
tgtcgtcagc tcgtgtcgtg agatgttggg ttaagtcccg caacgagcgc aaccctgcc   1080
cttagttgcc agcgcgtaat ggtgggcact ctaagggac tgccgtcgat gaggcggagg   1140
aaggtgggga tgacgtcaaa tcatcatgcc ccttatgccc tgggctacac acgtgctaca  1200
atgggtgcta cagagggcgt gcgaaggcgc gagccggagc gaatcccaaa aaagcacccc  1260
cagttcggat tgcaggctgc aactcgcctg catgaagtcg gaatcgctag taatcgcgga  1320
tcagcatgcc gcggtgaata cgttcccggg ccttgtacac accgccgtc acaccatgag   1380
agtcagcaac acctgaagac acaggttaag ctgtgttgaa ggtgggctg atgattgggg   1440
tgaagtcgta acaaggtagc cgtacgggaa cgtgcggctg gatcaccctc ctttcta     1497
```

FIG. 5

**16SrDNA consensus sequence for *Caldicellulosiruptor* sp. BluCon085 (SEQ ID NO. 6)**

```
cgcatgcaag tcgagcggag atggtggttg aaggtgatga gctggaggct gccatcttag     60
cggcggacgg gtgagtaaca cgtgagcaac ctaccccag cacggggata acagctcgaa    120
agggctgcta atacccgatg ggaccacgtc atcgcatggt gatgtggtga aannnnnnnn    180
ggnngnnnnn nnggctgggg atgggctcgc ggccatcag ctagttggtg nggtaacggc     240
tnaccaaggc gacgacgggt agccggcctg agagggtgta cggccacagt gggactgaga    300
cacggcccac actcctacgg gaggcagcag cggggaatct tgcgcaatgg gcggaagcct    360
gacgcagcga cgccgcgtga gggaagaagc cttcgggt gtaaacctct ttggacgggg      420
agaagtagga gatagtaccc gtttaaaaag ccacggctaa ctacgtgcca gcagccgcgg    480
taatacgtag gtggcgagcg ttgtccggaa ttactgggcg taaagggtgc gtaggcggct    540
atgcgagtta agcgtgaaag ccttaggctc aacctaagga ttgcgcttaa tactgcatag    600
cttgagtgcg ggagaggacg gcggaattcc cggtgtagcg gtgaaatgcg tagatatcgg    660
gaggaacacc agtggcgaag gcggccgtct ggaccgtaac tgacgctgag gcacgaaagc    720
gtggggagcg aacaggatta gataccctgg tagtccacgc tgtaaacgat ggatgctagg    780
tgtggggag aaggactcnt ccgtgccgta gttaacacaa taagcatccc gcctggggag    840
tacggccgca aggttgaaac tcaaaggaat tgacggggggc ccgcacaagc ggtggagcat    900
gtggtttaat tcgaagcaac gcgaagaacc ttaccagggc ttgacatgcc ggggacctgc    960
ccgaaagggt ggggtgcctg ttcgatgaga gcaggagccc ggacacaggt ggtgcatggt   1020
tgtcgtcagc tcgtgtcgtg agatgttggg ttaagtcccg caacgagcgc aaccctgcc   1080
cttagttgcc agcgcgtaat ggtgggcact ctaaggggac tgccgtcgat gaggcggagg   1140
aaggtgggga tgacgtcaaa tcatcatgcc ccttatgccc tgggctacac acgtgctaca   1200
atgggtgcta cagagggcgt gcgaaggcgc gagccggagc gaatcccaaa aaagcacccc   1260
cagttcggat tgcaggctgc aactcgcctg catgaagtcg gaatcgctag taatcgcgga   1320
tcagcatgcc gcggtgaata cgttcccggg ccttgtacac accgcccgtc acaccatgag   1380
agtcagcaac acctgaagac acaggttaag ctgtgttgaa ggtgggctg atgattgggg   1440
tgaagtcgta acaaggtagc cgtacgggaa cgtgcggctg gatcaccctc ctttcta      1497
```

FIG. 6

**16SrDNA consensus sequence for *Caldicellulosiruptor* sp. BluConL70 (SEQ ID NO. 7)**

```
cgcatgcaag tcgagcggag atggtggttg aaggtgatga gctggaggct gccatcttag     60
cggcggacgg gtgagtaaca cgtgagcaac ctaccccag cacggggata acagctcgaa    120
agggctgcta ataccgatg ggaccacgtc atcgcatggt gatgtggtga aannnnnnnn    180
ggnngnnnnn nnggctgggg atgggctcgc ggcccatcag ctagttggtg nggtaacggc    240
tnaccaaggc gacgacgggt agccggcctg agagggtgta cggccacagt gggactgaga    300
cacggcccac actcctacgg gaggcagcag cggggaatct tgcgcaatgg gcggaagcct    360
gacgcagcga cgccgcgtga gggaagaagc ccttcggggt gtaaacctct ttggacgggg    420
agaagtagga gatagtaccc gtttaaaaag ccacggctaa ctacgtgcca gcagccgcgg    480
taatacgtag gtggcgagcg ttgtccggaa ttactgggcg taaagggtgc gtaggcggct    540
atgcgagtta agcgtgaaag ccttaggctc aacctaagga ttgcgcttaa tactgcatag    600
cttgagtgcg ggagaggacg gcggaattcc cggtgtagcg gtgaaatgcg tagatatcgg    660
gaggaacacc agtggcgaag gcggccgtct ggaccgtaac tgacgctgag gcacgaaagc    720
gtggggagcg aacaggatta gataccctgg tagtccacgc tgtaaacgat ggatgctagg    780
tgtgggggag aaggactcnt ccgtgccgta gttaacacaa taagcatccc gcctggggag    840
tacggccgca aggttgaaac tcaaaggaat tgacggggc ccgcacaagc ggtggagcat    900
gtggtttaat tcgaagcaac gcgaagaacc ttaccagggc ttgacatgcc ggggacctgc    960
ccgaaagggt ggggtgcctg ttcgatgaga gcaggagccc ggacacaggt ggtgcatggt   1020
tgtcgtcagc tcgtgtcgtg agatgttggg ttaagtcccg caacgagcgc aaccccctgcc   1080
cttagttgcc agcgcgtaat ggtgggcact ctaagggac tgccgtcgat gaggcggagg   1140
aaggtgggga tgacgtcaaa tcatcatgcc ccttatgccc tgggctacac acgtgctaca   1200
atgggtgcta cagagggcgt gcgaaggcgc gagccggagc gaatcccaaa aaagcacccc   1260
cagttcggat tgcaggctgc aactcgcctg catgaagtcg gaatcgctag taatcgcgga   1320
tcagcatgcc gcggtgaata cgttcccggg ccttgtacac accgcccgtc acaccatgag   1380
agtcagcaac acctgaagac acaggttaag ctgtgttgaa ggtggggctg atgattgggg   1440
tgaagtcgta acaaggtagc cgtacgggaa cgtgcggctg gatcaccctc ctttcta     1497
```

FIG. 7

**16SrDNA consensus sequence for *Caldicellulosiruptor* sp. BluConL60 (SEQ ID NO. 8)**

```
catgcagtcg agcggagatg gtggttgaag gtgatgagct ggaggctgcc atcttagcgg    60
cggacgggtg agtaacacgt gagcaaccta cccccagcac ggggataaca gctcgaaagg   120
gctgctaata cccgatggga ccacgtcatc gcatggtgat gtggtgaaag ggctggggat   180
gggctcgcgg cccatcagct agttggtgng gtaacggctn accaaggcga cgacgggtag   240
ccggcctgag agggtgtacg gccacagtgg gactgagaca cggcccacac tcctacggga   300
ggcagcagcg gggaatcttg cgcaatgggc ggaagcctga cgcagcgacg ccgcgtgagg   360
gaagaagccc ttcggggtgt aaacctcttt ggacggggag aagtaggaga tagtacccgt   420
ttaaaaagcc acggctaact acgtgccagc agccgcggta atacgtaggt ggcgagcgtt   480
gtccggaatt actgggcgta aagggtgcgt aggcggctat gcgagttaag cgtgaaagcc   540
ttaggctcaa cctaaggatt gcgcttaata ctgcatagct tgagtgcggg agaggacggc   600
ggaattcccg gtgtagcggt gaaatgcgta gatatcggga ggaacaccag tggcgaaggc   660
ggccgtctgg accgtaactg acgctgaggc acgaaagcgt gggagcgaa caggattaga   720
taccctggta gtccacgctg taaacgatgg atgctaggtg tggggagaa ggactcntcc   780
gtgccgtagt taacacaata agcatcccgc ctggggagta cggccgcaag gttgaaactc   840
aaaggaattg acggggcccc gcacaagcgg tggagcatgt ggtttaattc gaagcaacgc   900
gaagaacctt accagggctt gacatgccgg ggacctgccc gaaagggtgg ggtgcctgtt   960
cgatgagagc aggagcccgg acacaggtgg tgcatggttg tcgtcagctc gtgtcgtgag  1020
atgttgggtt aagtcccgca acgagcgcaa ccctgccct tagttgccag cgcgtaatgg  1080
tgggcactct aaggggactg ccgtcgatga ggcggaggaa ggtgggatg acgtcaaatc  1140
atcatgcccc ttatgccctg ggctacacac gtgctacaat gggtgctaca gagggcgtgc  1200
gaaggcgcga gcggagcga atcccaaaaa agcacccca gttcggattg caggctgcaa  1260
ctcgcctgca tgaagtcgga atcgctagta atcgcggatc agcatgccgc ggtgaatacg  1320
ttcccgggcc ttgtacacac cgcccgtcac accatgagag tcagcaacac ctgaagacac  1380
aggttaagct gtgttgaagg tggggctgat gattggggtg aagtcgtaac aaggtagccg  1440
tacgggaacg tgcggctgga tcacctcctt tct
```

FIG. 8

EXTREME THERMOPHILIC BACTERIA OF THE GENUS *CALDICELLULOSIRUPTOR* SUITABLE FOR THE CONVERSION OF CELLULOSIC AND STARCHY BIOMASS

TECHNICAL FIELD

The present disclosure pertains to novel isolated cellulolytic extreme thermophilic bacterial cells belonging to the genus *Caldicellulosiruptor*, mutants thereof, isolated strains, microbial cultures and microbial compositions. The novel bacteria are in particular suitable for the production of fermentation products such as lactic acid from any carbon source, not limited to cellulosic material but especially useful for converting cellulosic biomass like ligniocellulosic biomass and/or starch containing biomass.

BACKGROUND

Various carbohydrates, such as cellulosic and lignocellulosic materials, e.g. in fibrous form, are produced, processed, and used in large quantities in a number of applications. Often such materials are used once, and then discarded as waste, or are simply considered to be waste materials, e.g., sewage, bagasse, sawdust, and stover.

In general, fermentation products are produced by degradation of carbon-based biomass like starch-containing material into fermentable sugars by liquefaction and saccharification followed by conversion of the sugars directly or indirectly into the desired fermentation product using a fermenting organism.

However, the industry of producing fermentation products such as ethanol and lactic acid is facing the challenge of redirecting the production process from fermentation of relatively easily convertible but expensive starchy materials, to the complex but inexpensive cellulosic waste or lignocellulosic biomass such as plant biomass.

Normally starch containing substrates are more costly than lignocellulosic substrates but in certain cases starch containing substrates may be side streams of other production processes and available for further processing into lactic acid or other products like ethanol at advantageous costs Unlike starch, which contains homogenous and easily hydrolysed polymers, lignocellulosic biomass contains variable amounts of cellulose, hemicellulose, lignin and small amounts of protein, pectin, wax and other organic compounds. Lignocellulosic biomass should be understood in its broadest sense, so that it apart from wood, agricultural residues, energy crops also comprises different types of waste from both industry and households. Cellulosic biomass is a vast poorly exploited resource, and in some cases a waste problem. However, hexoses from cellulose can be converted by yeast or other microorganisms to ethanol for which there is a growing demand.

Typically, the first step in utilization of lignocellulosic biomass is a pre-treatment step, in order to fractionate the components of lignocellulosic material and increase their surface area.

The pre-treatment method most often used is steam pretreatment, a process comprising heating of the lignocellulosic material by steam injection to a temperature of 130-230° C. Prior to or during steam pretreatment, a catalyst like mineral or organic acid or a caustic agent facilitating disintegration of the biomass structure can be added optionally.

Another type of lignocellulose hydrolysis is acid hydrolysis, where the lignocellulosic material is subjected to an acid such as sulphuric acid whereby the sugar polymers cellulose and hemicellulose are partly or completely hydrolysed to their constituent sugar monomers and the structure of the biomass is destroyed facilitating access of hydrolytic enzymes in subsequent processing steps.

Alkali pretreatment typically uses NaOH or KOH and increases the degradation of hemicellulose and lignin. During alkali pretreatment, the acetate group from the hemicellulose is removed, making hydrolytic enzymes more easily accessible to carbohydrates. By solubilizing the lignin by the alkali addition accessibility of the enzymes in the microorganisms to the cellulose and hemicellulose will be increased.

A further method is wet oxidation wherein the material is treated with oxygen at 150-185° C. Either pretreatment can be followed by enzymatic hydrolysis to complete the release of sugar monomers. This pre-treatment step results in the hydrolysis of cellulose into glucose while hemicellulose is transformed into the pentoses xylose and arabinose and the hexoses glucose, mannose and galactose. Thus, in contrast to starch, the hydrolysis of lignocellulosic biomass results in the release of pentose sugars in addition to hexose sugars. This implies that useful fermenting organisms need to be able to convert both hexose and pentose sugars to desired fermentation products such as ethanol.

After the pre-treatment the lignocellulosic biomass processing schemes involving enzymatic or microbial hydrolysis commonly involve four biologically mediated transformations: (1) the production of saccharolytic enzymes (cellulases and hemicellulases); (2) the hydrolysis of carbohydrate components present in pretreated biomass to sugars; (3) the fermentation of hexose sugars (e.g. glucose, mannose, and galactose); and (4) the fermentation of pentose sugars (e.g., xylose and arabinose).

Each processing step can make the overall process more costly and, therefore, decrease the economic feasibility of producing biofuel or carbon-based chemicals from cellulosic biological material. Thus, there is a need to develop methods that reduce the number of processing steps needed to convert cellulosic biological material to biofuel and other commercially desirable materials.

The four biologically mediated transformations may occur in a single step in a process configuration called consolidated bioprocessing (CBP), which is distinguished from other less highly integrated configurations in that CBP does not involve a dedicated process step for cellulase and/or hemicellulase production. CBP offers the potential for higher efficiency than a processes requiring dedicated cellulase production in a distinct unit operation.

Complex starchy raw materials used for the production of desired fermentation products like lactic acid are subjected to pretreatment by gelatinization and liquefaction. Starch gelatinization is a process of breaking down the intermolecular bonds of starch molecules in the presence of water and heat, allowing the hydrogen bonding sites (the hydroxyl hydrogen and oxygen) to engage more water. This irreversibly dissolves the starch granule in water. Water acts as a plasticizer. Three main processes happen to the starch granule: granule swelling, crystal or double helical melting, and amylose leaching. During heating, water is first absorbed in the amorphous space of starch, which leads to swelling phenomenon. Water then enters via amorphous regions the tightly bound areas of double helical structures of amylopectin. Heat causes such regions to become diffuse, the amylose chains begin to dissolve, to separate into an amorphous form and the number and size of crystalline regions decreases.

Penetrated water increases the randomness in the starch granule structure, and causes swelling; eventually amylose molecules leach into the surrounding water and the granule structure disintegrates.

Gelatinization improves the availability of starch for amylase hydrolysis leading to liquefaction. Therefore, gelatinization and liquefaction of starchy raw materials like corn are used for decades in fermentation processes like in the first generation production of the carbon-based chemical ethanol.

Therefore, the availability of novel microorganisms for converting lignocellulosic biomass material and/or starch containing biomass to carbon-based chemicals would be highly advantageous.

SUMMARY OF THE DISCLOSURE

The present invention relates to novel microorganisms and compositions useful for processing carbohydrate-containing materials.

Carbohydrate-containing materials (e.g., biomass materials or biomass-derived materials, such as starchy materials (starch), cellulosic materials, lignocellulosic materials, or biomass materials that are or that include significant amounts of low molecular weight sugars (e.g., monosaccharides, disaccharides, or trisaccharides), can be processed to change their structure, and products can be made from the structurally changed materials. For example, many of the methods described herein can provide cellulosic and/or lignocellulosic materials that have a lower molecular weight and/or crystallinity relative to a native material. Many of the methods provide materials that can be more readily utilized by a variety of microorganisms to produce useful products, such as hydrogen, alcohols (e.g., ethanol or butanol), organic acids (e.g., lactic acid), hydrocarbons, co-products (e.g., proteins) or mixtures of any of these.

In a first aspect, embodiments of the disclosure provide novel isolated thermophilic bacterial cells belonging to the genus *Caldicellulosiruptor*, in particular capable of producing high levels of lactic acid from cellulosic and/or starch containing biomass.

In one aspect, embodiments of this disclosure relate to the *Caldicellulosiruptor* sp. strain BluConL70 listed in Table 1 was deposited on Mar. 20, 2020 under the accession number DSM DSM 33496 according to the requirements of the Budapest Treaty, accepted and publicly available at the Deutsche Sammlung von Mikroorganismen und Zellkulturen (DSMZ), Inhoffenstraße 7B, 38124 Braunschweig (DE) by BluCon Biotech GmbH, Nattermannallee 1, 50829 Cologne (DE).

In one aspect, embodiments of this disclosure relate to the *Caldicellulosiruptor* sp. strain BluConL60 that was deposited on Aug. 29, 2019 under the accession number DSM 33252 according to the requirements of the Budapest Treaty, accepted and publicly available at the Deutsche Sammlung von Mikroorganismen und Zellkulturen (DSMZ), Inhoffenstraße 7B, 38124 Braunschweig (DE) by BluCon Biotech GmbH, Nattermannallee 1, 50829 Cologne (DE).

In one aspect, embodiments of this disclosure relate to the *Caldicellulosiruptor* sp strain BluConL085 listed in Table 1 was deposited on Mar. 10, 2020 under the accession number DSM BluCon085 according to the requirements of the Budapest Treaty, accepted and publicly available at the Deutsche Sammlung von Mikroorganismen und Zellkulturen (DSMZ), Inhoffenstraße 7B, 38124 Braunschweig (DE) by BluCon Biotech GmbH, Nattermannallee 1, 50829 Cologne (DE).

In one aspect, embodiments of this disclosure relate to the *Caldicellulosiruptor* sp strain BluConL052 listed in Table 1 was deposited on Mar. 10, 2020 under the accession number DSM DSM 33470 according to the requirements of the Budapest Treaty, accepted and publicly available at the Deutsche Sammlung von Mikroorganismen und Zellkulturen (DSMZ), Inhoffenstraße 7B, 38124 Braunschweig (DE) by BluCon Biotech GmbH, Nattermannallee 1, 50829 Cologne (DE).

In one aspect, embodiments of this disclosure relate to the *Caldicellulosiruptor* sp strain BluCon016 listed in Table 1 was deposited on Apr. 9, 2019 under the accession number DSM 33097 according to the requirements of the Budapest Treaty, accepted and publicly available at the Deutsche Sammlung von Mikroorganismen und Zellkulturen (DSMZ), Inhoffenstraße 7B, 38124 Braunschweig (DE) by BluCon Biotech GmbH, Nattermannallee 1, 50829 Cologne (DE).

In one aspect, embodiments of this disclosure relate to the *Caldicellulosiruptor* sp strain BluConL014 listed in Table 1 was deposited on Apr. 9, 2019 under the accession number DSM 33096 according to the requirements of the Budapest Treaty, accepted and publicly available at the Deutsche Sammlung von Mikroorganismen und Zellkulturen (DSMZ), Inhoffenstraße 7B, 38124 Braunschweig (DE) by BluCon Biotech GmbH, Nattermannallee 1, 50829 Cologne (DE).

In one aspect, embodiments of this disclosure relate to the *Caldicellulosiruptor* sp strain BluCon006 listed in Table 1 was deposited on Apr. 9, 2019 under the accession number DSM 33095 according to the requirements of the Budapest Treaty, accepted and publicly available at the Deutsche Sammlung von Mikroorganismen und Zellkulturen (DSMZ), Inhoffenstraße 7B, 38124 Braunschweig (DE) by BluCon Biotech GmbH, Nattermannallee 1, 50829 Cologne (DE).

TABLE 1

*Caldicellulosiruptor* sp. strains

| Genus | Species | Name | DSMZ accession number | Deposition date |
| --- | --- | --- | --- | --- |
| Caldicellulosiruptor | sp | BluConL70 | DSM 33496 | Mar. 20, 2020 |
| Caldicellulosiruptor | sp | BluCon085 | DSM 33485 | Mar. 10, 2020 |
| Caldicellulosiruptor | sp | BluCon052 | DSM 33470 | Mar. 10, 2020 |
| Caldicellulosiruptor | sp | BluCon006 | DSM 33095 | Apr. 9, 2019 |
| Caldicellulosiruptor | sp | BluCon014 | DSM 33096 | Apr. 9, 2019 |
| Caldicellulosiruptor | sp | BluCon016 | DSM 33097 | Apr. 9, 2019 |
| Caldicellulosiruptor | sp | BluConL60 | DSM 33252 | Aug. 29, 2019 |

In still another aspect, the present invention relates to an isolated strain comprising a *Caldicellulosiruptor* sp. cell according to any of the preceding aspects.

In a further aspect, embodiments of this disclosure relate to microorganism of the strain *Caldicellulosiruptor* sp. BluConL60 (DSMZ Accession number 33252), BluConL70 (DSMZ Accession number 33496), BluCon085 (DSMZ Accession number 33485), BluCon052 (DSMZ Accession number 33470, BluCon016 (DSMZ Accession number 33097), BluCon014 (DSMZ Accession number 33096) or BluCon006 (DSMZ Accession number 33095), microorganism derived therefrom, progenies or mutants thereof, wherein the mutants thereof retaining the properties of BluConL60, BluConL70, BluCon085, BluCon052, BluCon016, BluCon014 or BluCon006.

In another aspect, the present disclosure relates to a method of producing a fermentation product comprising culturing a cell according to the disclosure or a strain according to the disclosure under suitable conditions.

In still another aspect, embodiments of this disclosure relate to methods for converting a carbohydrate-containing material like starch, hemicellulose, lignocellulosic and/or cellulosic biomass material, starch and/or hemicellulose to a carbon-based chemical, in particular lactic acid and/or a salt or an ester thereof, comprising the step of contacting the lignocellulosic and/or cellulosic biomass material with a microbial culture for a period of time at an initial temperature and an initial pH, thereby producing an amount of a carbon-based products, in particular lactic acid and/or a salt or an ester thereof; wherein the microbial culture comprises an extremely thermophilic microorganism of the genus *Caldicellulosiruptor*, in particular all microorganisms of the strain *Caldicellulosiruptor* sp. as listed in table 1 with their respective deposition numbers, microorganisms derived from either of these strains or mutants or homologues thereof, in particular mutants thereof retaining the properties.

In still another aspect, embodiments of this disclosure relate to methods of making lactic acid from a carbon-based biomass like starch, hemicellulose, lignocellulosic and/or cellulosic biomass material, wherein the method comprises combining a microbial culture and the biomass in a medium; and fermenting the biomass under conditions and for a time sufficient to produce lactic acid, a salt or an ester thereof, in a single step process as part of a consolidated bioprocessing (CBP) system, with a cell, strain, microbial culture and/or a microorganism according to the present disclosure under suitable conditions, in particular using mutants thereof retaining the properties.

In still another aspect, embodiments of this disclosure relate to methods of making both ethanol and lactic acid from biomass material, wherein the method comprises combining a microbial culture and the biomass in a medium; and fermenting the biomass under conditions and for a time sufficient to produce ethanol and lactic acid, a salt or an ester of the latter, in a single step process as part of a consolidated bioprocessing (CBP) system, with a cell, strain, microbial culture and/or a microorganism or mutants thereof retaining the properties according to the present disclosure under suitable conditions.

In still another aspect, embodiments of this disclosure relate to methods of making lactic acid from biomass material, wherein the method comprises combining a microbial culture and the biomass in a medium; and fermenting the biomass under conditions and for a time sufficient to produce ethanol and/or lactic acid, and/or acetic acid, a salt or an ester of the latter, in a single step process as part of a consolidated bioprocessing (CBP) system, with a cell, strain, microbial culture and/or a microorganism according to the present disclosure under suitable conditions.

Further, embodiments of this disclosure relate to compositions for converting carbon-based biomass material like lignocellulosic biomass or a microbial culture comprising a cell, strain or microorganism according to the present disclosure.

Further, embodiments of this disclosure relate to the use of a cell, strain, microorganism and/or a microbial culture according to the present disclosure for the production of lactic acid, a salt or an ester thereof or for the production of ethanol.

Further, embodiments of this disclosure relate to a lactic acid production procedure, characterized in that it includes the following steps:
  a) converting starch and/or starch-containing material to lactic acid in a single step process as part of a consolidated bioprocessing (CBP) system in a bioreactor by a microorganism listed in Table 1 of the present description, microorganism derived therefrom, progenies or mutants thereof, wherein the mutants thereof retaining the properties of a microorganism listed in Table 1 of the present description,
  b) separation of lactic acid from the fermentation medium
  c) purification of lactic acid.

Further, embodiments of this disclosure relate to a fermentation process for the production of lactic acid comprising the steps of contacting modified starch and/or modified starch-containing material with a microbial culture comprising an isolated strain according to the present disclosure for a period of time at an initial temperature and an initial pH, thereby producing an amount of a lactic acid, wherein the modified starch and/or the modified starch-containing material is converted in a single step process as part of a consolidated bioprocessing (CBP) system and wherein in particular the lactic acid is separated during and/or after the conversion.

Before the disclosure is described in detail, it is to be understood that this disclosure is not limited to the particular component parts of the devices described or process steps of the methods described and methods may vary. It is also to be understood that the terminology used herein is for purposes of describing particular embodiments only, and is not intended to be limiting. It must be noted that, as used in the specification and the appended claims, the singular forms "a," "an" and "the" include singular and/or plural referents unless the context clearly dictates otherwise. It is moreover to be understood that, in case parameter ranges are given which are delimited by numeric values, the ranges are deemed to include these limitation values.

To provide a comprehensive disclosure without unduly lengthening the specification, the applicant hereby incorporates by reference each of the patents and patent applications cited herein.

BRIEF DESCRIPTION OF THE DRAWINGS

FIG. 1 shows a 16S rDNA from *Caldicellulosiruptor* sp. BluCon006 cell.

FIG. 2 shows a 16S rDNA from *Caldicellulosiruptor* sp. BluCon014 cell.

FIG. 3 shows a 16S rDNA from *Caldicellulosiruptor* sp. BluCon016 cell.

FIG. 4 shows a 16S rDNA from *Caldicellulosiruptor* sp. DIB104C cell.

FIG. 5 shows a 16S rDNA from *Caldicellulosiruptor* sp. BluCon052 cell.

FIG. 6 shows a 16S rDNA from *Caldicellulosiruptor* sp. BluCon085 cell.

FIG. 7 shows a 16S rDNA from *Caldicellulosiruptor* sp. BluConL70 cell.

FIG. 8 shows a 16S rDNA from *Caldicellulosiruptor* sp. BluConL60 cell.

DETAILED DESCRIPTION OF THIS DISCLOSURE

Figure 9:
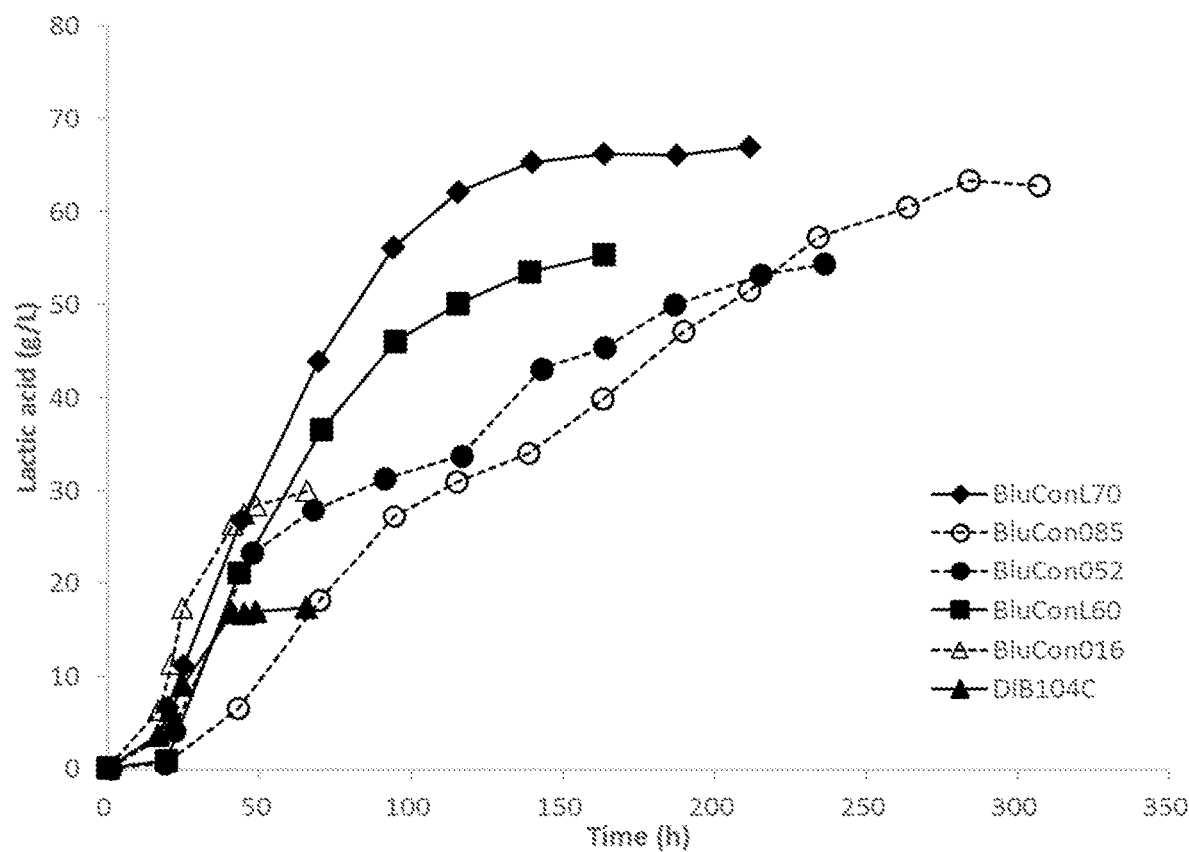
FIG. 9 is a diagram showing the lactic acid concentrations as a function of fermentation time of batch fermentations with strains BluConL70, BluCon085, BluCon052, BluConL60, BluCon016 and DIB104C with crystalline cellulose.
Figure 10:
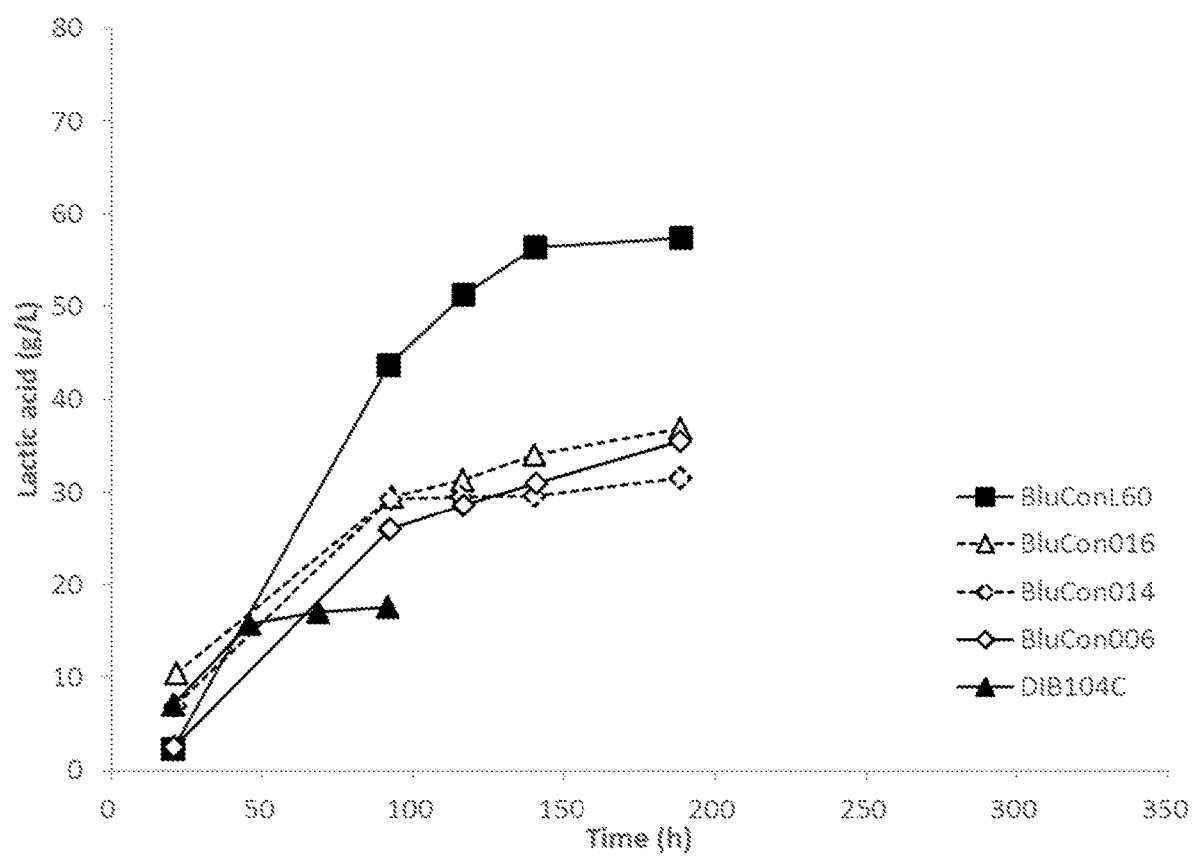
FIG. 10 is a diagram showing the lactic acid concentrations as a function of fermentation time of batch fermentations with strains BluConL60, BluCon016, BluCon014, BluCon016 and DIB104C with crystalline cellulose.

The present disclosure relates to methods, microorganisms, and compositions useful for processing cellulosic biomass like lignocellulosic biomass and/or starch containing biomass. The disclosure relates, in certain aspects, to microorganisms which are able to convert pretreated lignocellulosic biomass such as, for example pretreated miscanthus grass, to soluble products that can be used by the same or by another microorganism to produce an economically desirable product such as, for example, a carbon-based chemical, in particular lactic acid and/or a salt thereof.

An advantage property of the strains listed in Table 1 is the higher lactic acid concentrations in same time intervals and lower acetic acid and ethanol concentrations in the fermentation from starch contain biomass and/or cellulosic biomass like lignocellulosic biomass. The strains of table 1 could be used one or for both conversion processes. Surprisingly, the *Caldicellulosiruptor* sp. of table 1 according to the present disclosure are cellulolytic as well as amylolytic active.

The application of this technology has the potential to render production of carbon-based chemicals more economically feasible and to allow a broader range of microorganisms to utilize recalcitrant biomass. The use of cellulosic materials as sources of bioenergy is currently limited by typically requiring preprocessing of the cellulosic material. Such preprocessing methods can be expensive. Thus, methods that reduce dependence on preprocessing of cellulosic materials may have a dramatic impact on the economics of the use of recalcitrant biomass for carbon-based chemicals production. One challenge in converting biomass into fermentation products is the recalcitrance and heterogeneity of the biological material.

The present inventors have found microorganisms of the genus *Caldicellulosiruptor* which have a variety of advantageous properties for their use in the conversion of starch containing biomass/material and/or lignocellulosic biomass material to carbon-based chemicals, preferably to lactic acid and/or a salt thereof, preferably in a single step process as part of a consolidated bioprocessing (CBP) system.

In particular, these microorganisms are extremely thermophilic and show broad substrate specificities and high natural production of lactic acid. Moreover, ethanol and lactic acid fermentation at high temperatures, for example over 70° C. has many advantages over mesophilic fermentation. One advantage of thermophilic fermentation is the minimization of the problem of contamination in batch cultures, fed-batch cultures or continuous cultures, since only a few microorganisms are able to grow at such high temperatures in un-detoxified lignocellulose biomass material.

It is also an advantage that the cells, strains and microorganisms according to the present disclosure grow on pre-treated as well as on untreated lignocellulosic biomass material. Furthermore, the cells, strains and microorganisms according to the present disclosure produces high lactic acid concentrations and low acetic acid and ethanol concentrations in fermentation processes by converting starch containing biomass/material.

In particular, the strains of table 1 produces high lactic acid concentrations after a cultivation time of 40 hours or more, in particular after 60 hours, in particular after 71 hours, in particular after 90 hours.

In the present context, the term "starch-containing biomass" or "starch-containing material" includes in particular starch-containing plant material, including: tubers, roots, whole grain; and any combination thereof. The starch-containing biomass/material may be obtained from cereals. Suitable starch-containing biomass/material includes corn (maize), wheat, barley, cassava, sorghum, rye, potato, or any combination thereof. Corn is the preferred feedstock, especially when the fermentation product is ethanol. The starch-containing material may also consist of or comprise, e.g., a side stream from starch processing, e.g., C6 carbohydrate containing process streams that may not be suited for production of syrups. Whole stillage typically contains about 10-15 wt-% dry solids. Whole stillage components include fiber, hull, germ, oil and protein components from the starch-containing feedstock as well as non-fermented starch.

Starch containing material can be distinguished between native starch materials, also designated raw starch materials, are unmodified and unprocessed starch material, whereas modified starch materials are starch materials obtained by physical, enzymatic or chemical processes, which lead to changes of physicochemical properties like moisture content, amylose content, swelling and viscosity and other parameters (Karmakar et al., 2014).

Native and modified starch-containing materials (e.g., biomass materials or biomass-derived materials, such as native starchy materials (native starch), or biomass materials that include significant amounts of low molecular weight sugars, which are degradation products of native or modified starch (e.g., monosaccharides, disaccharides, or trisaccharides), can be processed to change their structure, and products can be made from the structurally changed materials.

For example, many of the methods described herein can provide starch-containing materials that have a lower molecular weight and/or crystallinity relative to a native material. Many of the methods provide materials that can be more readily utilized by a variety of microorganisms to produce useful products, such as organic acids (e.g., lactic acid), hydrogen, alcohols (e.g., ethanol or butanol), hydrocarbons, co-products (e.g., proteins) or mixtures of any of these.

As used herein "unmodified starch" or "unmodified starch-containing material" or "native starch" refers to unmodified and unprocessed starch material which are not obtained by physical treatment including heat treatment, enzymatic or chemical processes, which lead to changes of physicochemical properties like moisture content, amylose content, swelling and viscosity and other parameters (Karmakar et al., 2014). Therefore, as used herein "modified starch" or "modified starch-containing material" refers to modified and processed starch material which are obtained by physical treatment including heat treatment, enzymatic or chemical processes, which lead to changes of physicochemical properties like moisture content, amylose content, swelling and viscosity and other parameters. In an advantageous embodiment, the starch and/or the starch containing material is heat treated before the fermentation process.

The microorganisms according to the present disclosure can grow efficiently on native and modified starch. The main product when grown on untreated biomass substrates is lactic acid.

Cellulosic biomass, sometimes called lignocellulosic biomass, is a heterogeneous complex of carbohydrate polymers (cellulose and hemicellulose) and lignin, a complex polymer of phenylpropanoid units. Biomass includes substantial amounts of cellulose (30-50%), hemicellulose (10-35%) and lignin (5-30%). Cellulose and hemicellulose are useful for conversion into C5 and C6 sugars which can further be converted to either fuels such as bioethanol or chemicals such as furfural, HMF, leuvinic acid, and lignin can be thermochemically depolymerised to platform chemicals such as phenolics and styrene. In addition to ethanol, many more chemicals and chemical feedstocks are potential products from renewable plant biomass.

The term "cellulose" is intended to mean a linear homopolysaccharide derived from biomass (encompassing organic matter of plant origin, algae included, cellulose of animal origin and also cellulose of bacterial origin) and consisting of units (or rings) of glucose (D-anhydroglucopyranose—AGU for "anhydro glucose unit") which are linked to one another by β-(1-4) glycosidic bonds. The repeat unit is a glucose dimer also known as cellobiose dimer. The structure of cellulose consists of parallel D-glucose chains. The structure is stabilized by hydrogen bonds giving it fibrous properties. The cellulose substrate may be in paper sheet, pulp form, tablet, or a cellulose powder prepared by either mechanical or chemical disintegration of alpha-cellulose, hard or soft wood pulp, purified wood pulp, cotton linter sheet, cotton pulp, or the like. Other sources of cellulose include low crystallinity celluloses and commercially available cellulose excipients, such as microfibrillated cellulose, powdered cellulose, regenerated cellulose, and microcrystalline cellulose. In certain embodiments the cellulose substrate may include Microcrystalline cellulose is a crystalline, powdery substance, obtained by means of the controlled hydrolysis of α-cellulose, whose characteristics are well known and are described, for example, in the book by R. C. Rowe, P. J. Sheskey and P. J. Weller, Handbook of pharmaceutical excipients, fourth edition, Pharmaceutical Press, 2003. Microcrystalline cellulose is a crystalline, powdery substance, obtained by means of the controlled hydrolysis of α-cellulose, whose characteristics are well known and are described, for example, in the book by R. C. Rowe, P. J. Sheskey and P. J. Weller, Handbook of pharmaceutical excipients, fourth edition, Pharmaceutical Press, 2003.

In the present context the term "lignocellulosic biomass" is intended to designate a untreated lignocellulosic biomass and/or a lignocellulosic biomass material which has been subjected to a pretreatment step whereby lignocellulosic material has been at least partially separated into cellulose, hemicellulose and lignin thereby having increased the surface area and/or accessibility of the material. The lignocellulosic material may typically be derived from plant material, such as straw, hay, perennial grass, garden refuse, comminuted wood, fruit hulls and seed hulls.

The pretreatment method most often used is steam pretreatment, a process comprising heating of the lignocellulosic material by steam injection to a temperature of 130-230 degrees centigrade with or without subsequent sudden release of pressure. Prior to or during steam pretreatment, a catalyst like a mineral or organic acid or a caustic agent facilitating disintegration of the biomass structure can be added optionally. Catalysts often used for such a pretreatment include but are not limited to sulphuric acid, *sulphurous* acid, hydrochloric acid, acetic acid, lactic acid, sodium hydroxide (caustic soda), potassium hydroxide, calcium hydroxide (lime), ammonia or the respective salts or anhydrides of any of these agents.

Such steam pretreatment step may or may not be preceded by another treatment step including cooking of the biomass in water or steaming of the biomass at temperatures of 100-200° C. with or without the addition of a suitable catalyst like a mineral or organic acid or a caustic agent facilitating disintegration of the biomass structure. In between the cooking step and the subsequent steam pretreatment step one or more liquid-solid-separation and washing steps can be introduced to remove solubilized biomass components in order to reduce or prevent formation of inhibitors during the subsequent steam pretreatment step. Inhibitors formed during heat or steam pretreatment include but are not limited to furfural formed from monomeric pentose sugars, hydroxymethylfurfural formed from monomeric hexose sugars, acetic acid, levulinic acid, phenols and phenol derivatives.

Another type of lignocellulose hydrolysis is acid hydrolysis, where the lignocellulosic material is subjected to an acid such as sulfuric acid or sulfurous acid whereby the sugar polymers cellulose and hemicellulose are partly or completely hydrolysed to their constituent sugar monomers. A third method is wet oxidation wherein the material is treated with oxygen at 150-185 degrees centigrade. The pretreatments can be followed by enzymatic hydrolysis to complete the release of sugar monomers. This pre-treatment step results in the hydrolysis of cellulose into glucose while hemicellulose is transformed into the pentoses xylose and arabinose and the hexoses glucose, mannose and galactose. The pretreatment step may in certain embodiments be supplemented with treatment resulting in further hydrolysis of the cellulose and hemicellulose. The purpose of such an additional hydrolysis treatment is to hydrolyze oligosaccharide and possibly polysaccharide species produced during the acid hydrolysis, wet oxidation, or steam pretreatment of cellulose and/or hemicellulose origin to form fermentable sugars (e.g. glucose, xylose and possibly other monosaccharides). Such further treatments may be either chemical or enzymatic. Chemical hydrolysis is typically achieved by treatment with an acid, such as treatment with aqueous sulphuric acid or hydrochloric acid, at a temperature in the range of about 100-150 degrees centigrade. Enzymatic hydrolysis is typically performed by treatment with one or more appropriate carbohydrase enzymes such as cellulases, glucosidases and hemicellulases including xylanases.

It has been found that the microorganisms according to the present disclosure can grow efficiently on various types of pretreated and untreated biomass (e.g. wood incl. poplar, spruce and cotton wood; various types of grasses and grass residues incl. miscanthus, wheat straw, sugarcane bagasse, corn stalks, corn cobs, whole corn plants, sweet sorghum).

As used herein "efficient" growth refers to growth in which cells may be cultivated to a specified density within a specified time.

The microorganisms according to the present disclosure can grow efficiently on crystalline cellulose. The main product when grown on untreated biomass substrates was L-lactate.

The microorganisms according to the present disclosure also can grow efficiently on spent biomass—insoluble material that remains after a culture has grown to late stationary phase (e.g., greater than $10^8$ cells/mL) on untreated biomass.

Furthermore, the microorganisms according to the present disclosure grew efficiently on both the soluble and insoluble materials obtained after heat-treating the biomass.

The microorganisms according to the invention are anaerobic thermophile bacteria, and they are capable of growing at high temperatures even at or above 70 degrees centigrade. The fact that the strains are capable of operating at this high temperature is of high importance in the conversion of starch containing biomass and/or cellulosic like lignocellulosic material into fermentation products. The conversion rate of carbohydrates into e.g. lactic acid is much faster when conducted at high temperatures. For example, the volumetric ethanol productivity of a thermophilic *Bacillus* is up to ten-fold higher than a conventional yeast fermentation process which operates at 30 degrees centigrade Consequently, a smaller production plant is required for a given plant capacity, thereby reducing plant construction costs. As also mentioned previously, the high temperature reduces the risk of contamination from other microorganisms, resulting in less downtime and increased plant productivity. The high operation temperature may also facilitate the subsequent recovery of the resulting fermentation products.

Lignocellulosic biomass material and lignocellulose hydrolysates contain inhibitors such as furfural, phenols and carboxylic acids, which can potentially inhibit the fermenting organism. Therefore, it is an advantage of the microorganisms according to the present disclosure that they are tolerant to these inhibitors.

The microorganisms according to the present disclosure are novel species of the genus *Caldicellulosiruptor* or novel subspecies of *Caldicellulosiruptor saccharolyticus*.

For example, the genus *Caldicellulosiruptor* includes different species of extremely thermophilic (growth at temperature significantly above 70° C.) cellulolytic and hemicellulolytic strictly anaerobic nonsporeforming bacteria. The first bacterium of this genus, *Caldicellulosiruptor saccharolyticus* strain Tp8T 6331 (DSM 8903) has a temperature optimum of 70° C. and was isolated from a thermal spring in New Zealand (Rainey et al. 1994; Sissons et al. 1987). It hydrolyses a variety of polymeric carbohydrates with the production of acetate, lactate and trace amounts of ethanol (Donnison et al. 1988). Phylogenetic analysis showed that it constitutes a novel lineage within the *Bacillus/Clostridium* subphylum of the Gram-positive bacteria (Rainey et al. 1994).

According to the present disclosure, the microorganisms produce lactic acid and show several features that distinguish them from currently used microorganisms: (i) high yield and low product inhibition, (ii) simultaneous utilization of lignocellolytic biomass material and/or starch, and (iii) growth at elevated temperatures. The microorganisms according to the present disclosure are robust thermophile organisms with a decreased risk of contamination. They efficiently convert an extraordinarily wide range of biomass components to carbon-based chemicals like lactic acid.

As mentioned above, in one aspect, the present disclosure relates to isolated cells comprising a 16S rDNA sequence selected from the group consisting of SEQ ID NO 1, SEQ ID NO 2, SEQ ID NO 3, SEQ ID NO 5, SEQ ID NO 6, SEQ ID NO 7 and SEQ ID NO 8.

In one aspect, the present disclosure pertains to an isolated *Caldicellulosiruptor* sp. cell having a 16S rDNA sequence at least 99, at least 99.3, at least 99.5, at least, 99.7, at least 99.9, at least 99.99 percent identical to a sequence selected from the group consisting of SEQ ID NO 1, SEQ ID NO 2, SEQ ID NO 3, SEQ ID NO 5, SEQ ID NO 6, SEQ ID NO 7 and SEQ ID NO 8 and the properties of BluCon0L70, BluConL60, BluCon085, BluCon052, BluCon006, BluCon014 and/or BluCon016.

Each independently an embodiment of the invention is an isolated cell selected from the group consisting of *Caldicellulosiruptor* sp. BluConL70 having the DSMZ Accession number 33496, *Caldicellulosiruptor* sp. BluConL60 having the DSMZ Accession number 33252, *Caldicellulosiruptor* sp. BluCon085 having the DSMZ Accession number 33485 *Caldicellulosiruptor* sp. BluCon052 having the DSMZ Accession number 33470, *Caldicellulosiruptor* sp. BluCon006 having the DSMZ Accession number 33095, *Caldicellulosiruptor* sp. BluCon014 (DSMZ Accession number 33096) and *Caldicellulosiruptor* sp. BluCon016 (DSMZ Accession number 33097), microorganism derived therefrom, progenies or mutants thereof, wherein the mutants thereof retaining the properties of BluCon0L70, BluConL60, BluCon085, BluCon052, BluCon006, BluCon014 and/or BluCon016.

As used herein "mutant" or "homolog" means a microorganism derived from the cells or strains according to the present disclosure, which are altered due to a mutation. A mutation is a change produced in cellular DNA, which can be spontaneous, caused by an environmental factor or errors in DNA replication, or induced by physical or chemical conditions. The processes of mutation included in this and indented subclasses are processes directed to production of essentially random changes to the DNA of the microorganism including incorporation of exogenous DNA. All mutants of the microorganisms comprise the advantages of being extreme thermophile (growing and fermenting at temperatures above 70° C.) and are capable of fermenting lignocellulosic biomass to lactic acid, in particular to L-lactic acid. In an advantageous embodiment, mutants of the microorganisms according to the present disclosure have in a DNA-DNA hybridization assay, a DNA-DNA relatedness of at least 80%, preferably at least 90%, at least 95%, more preferred at least 98%, most preferred at least 99%, and most preferred at least 99.9% with an isolated bacterial strain *Caldicellulosiruptor* sp. selected from the group consisting of *Caldicellulosiruptor* sp. BluConL70 having the DSMZ Accession number 33496, *Caldicellulosiruptor* sp. BluConL60 having the DSMZ Accession number 33252, *Caldicellulosiruptor* sp. BluCon085 having the DSMZ Accession number 33485 *Caldicellulosiruptor* sp. BluCon052 having the DSMZ Accession number 33470, *Caldicellulosiruptor* sp. BluCon006 having the DSMZ Accession number 33095, *Caldicellulosiruptor* sp. BluCon014 (DSMZ Accession number 33096) and *Caldicellulosiruptor* sp. BluCon016 (DSMZ Accession number 33097). In particular, the mutants of a strain listed in table 1 retaining the properties of a strain listed in table 1, wherein in particular the properties are:

capable of growing in a medium comprising a lignocellulosic biomass and/or starch containing biomass, in particular wherein the strain is cellulolytic and amylolytic produce lactic acid, in particular more lactic acid compared to strains of the genus *Caldicellulosiruptor* having a level of 16S rDNA gene sequence similarity of at least 98%, preferably at least 99% or at least 99.5%, more preferably 100% to a 16S rDNA sequence selected from the group consisting of SEQ ID NO 1, SEQ ID NO 2, SEQ ID NO 3, SEQ ID NO 5, SEQ ID NO 6, SEQ ID NO 7 and SEQ ID NO 8.

produce more lactic acid compared to *Caldicellulosiruptor* sp. (DSM 25774), in particular in a fermentation time between 40 hours to 300 hours, in particular between 60 hours to 300 hours, in particular between 90 to 300 hours.

capable of surviving in high temperature conditions above 75° C.

The invention is based on an isolated bacterial strain, wherein the strain is selected from the group consisting of *Caldicellulosiruptor* sp. BluConL70 having the DSMZ Accession number 33496, *Caldicellulosiruptor* sp. BluConL60 having the DSMZ Accession number 33252, *Caldicellulosiruptor* sp. BluCon085 having the DSMZ Accession number 33485 *Caldicellulosiruptor* sp. BluCon052 having the DSMZ Accession number 33470, *Caldicellulosiruptor* sp. BluCon006 having the DSMZ Accession number 33095, *Caldicellulosiruptor* sp. BluCon014 (DSMZ Accession number 33096) and *Caldicellulosiruptor* sp. BluCon016 (DSMZ Accession number 33097), microorganism derived therefrom, progenies or mutants thereof, wherein the mutants thereof retaining the properties of BluCon0L70, BluConL60, BluCon085, BluCon052, BluCon006, BluCon014 and/or BluCon016 and contains 16S rDNA sequences at least 99 to 100%, preferably 99.5 to 99.99, more preferably at least 99.99 percent identical to a sequence selected from the group consisting of SEQ ID NO 1, SEQ ID NO 2, SEQ ID NO 3, SEQ ID NO 5, SEQ ID NO 6, SEQ ID NO 7 and SEQ ID NO 8.

The microorganisms of the species *Caldicellulosiruptor* sp. according to the present disclosure in particular refer to a microorganism which belongs to the genus *Caldicellulosiruptor* and which preferably has one or more of the following characteristics:

a) it is a microorganism of the genus *Caldicellulosiruptor*;
b) in a DNA-DNA hybridization assay, it shows a DNA-DNA relatedness of at least 70%, preferably at least 90%, at least 95%, more preferred at least 98%, most preferred at least 99% with either *Caldicellulosiruptor* sp. strain selected from the group consisting of *Caldicellulosiruptor* sp. BluConL70 having the DSMZ Accession number 33496, *Caldicellulosiruptor* sp. BluConL60 having the DSMZ Accession number 33252, *Caldicellulosiruptor* sp. BluCon085 having the DSMZ Accession number 33485 *Caldicellulosiruptor* sp. BluCon052 having the DSMZ Accession number 33470, *Caldicellulosiruptor* sp. BluCon006 having the DSMZ Accession number 33095, *Caldicellulosiruptor* sp. BluCon014 (DSMZ Accession number 33096) and *Caldicellulosiruptor* sp. BluCon016 (DSMZ Accession number 33097); and/or
c) it displays a level of 16S rDNA gene sequence similarity of at least 98%, preferably at least 99% or at least 99.5%, more preferably 100% with *Caldicellulosiruptor* sp. strain selected from the group consisting of *Caldicellulosiruptor* sp. BluConL70 having the DSMZ Accession number 33496, *Caldicellulosiruptor* sp. BluConL60 having the DSMZ Accession number 33252, *Caldicellulosiruptor* sp. BluCon085 having the DSMZ Accession number 33485 *Caldicellulosiruptor* sp. BluCon052 having the DSMZ Accession number 33470, *Caldicellulosiruptor* sp. BluCon006 having the DSMZ Accession number 33095, *Caldicellulosiruptor* sp. BluCon014 (DSMZ Accession number 33096) and *Caldicellulosiruptor* sp. BluCon016 (DSMZ Accession number 33097); and/or
d) it is capable of surviving in high temperature conditions above 75° C.
e) it is capable of surviving in high temperature conditions above 70° C., and or
f) it is a Gram-positive bacterium.

Preferably, at least two or at least three, and more preferred all of the above defined criteria a) to f) are fulfilled.

In an advantageous embodiment, the microorganisms according to the present disclosure in particular refer to a microorganism which belongs to the genus *Caldicellulosiruptor* and which preferably has one or more of the following characteristics:

a) It is a microorganism of the genus *Caldicellulosiruptor*
b) it is a microorganism of the species *Caldicellulosiruptor saccharolyticus;*
c) in a DNA-DNA hybridization assay, it shows a DNA-DNA relatedness of at least 80%, preferably at least 90%, at least 95%, more preferred at least 98%, most preferred at least 99%, and most preferred at least 99.9% with a sequence selected from the group consisting of SEQ ID NO 1, SEQ ID NO 2, SEQ ID NO 3, SEQ ID NO 5, SEQ ID NO 6, SEQ ID NO 7 and SEQ ID NO 8; and/or
d) it displays a level of 16S rDNA gene sequence similarity of at least 98%, preferably at least 99%, at least 99.5% or at least 99.7%, more preferably 99.99% with a sequence selected from the group consisting of SEQ ID NO 1, SEQ ID NO 2, SEQ ID NO 3, SEQ ID NO 5, SEQ ID NO 6, SEQ ID NO 7 and SEQ ID NO 8; and/or
e) it is capable of surviving and/or growing and/or producing a fermentation product selected from the group consisting of acids and alcohols at temperature conditions above 70° C., in particular of above 72° C.

Preferably, at least two or at least three, and more preferred all of the above defined criteria a) to e) are fulfilled.

The term "DNA-DNA relatedness" in particularly refers to the percentage similarity of the genomic or entire DNA of two microorganisms as measured by the DNA-DNA hybridization/renaturation assay according to De Ley et al. (1970) Eur. J. Biochem. 12, 133-142 or Hug et al. (1983) Syst. Appl. Microbiol. 4, 184-192. In particular, the DNA-DNA hybridization assay preferably is performed by the DSMZ (Deutsche Sammlung von Mikroorganismen und Zellkulturen GmbH, Braunschweig, Germany) Identification Service.

The term "16S rDNA gene sequence similarity" in particular refers to the percentage of identical nucleotides between a region of the nucleic acid sequence of the 16S ribosomal RNA (rDNA) gene of a first microorganism and the corresponding region of the nucleic acid sequence of the 16S rDNA gene of a second microorganism. Preferably, the region comprises at least 100 consecutive nucleotides, more preferably at least 200 consecutive nucleotides, at least 300 consecutive nucleotides or at least 400 consecutive nucleotides, most preferably about 480 consecutive nucleotides.

The strains according to the present disclosure have the potential to be capable of producing a number of different fermentation products, including acids, alcohols, ketones and hydrogen. In one embodiment, the alcohol is selected from ethanol, butanol, propanol, methanol, propanediol and butanediol. In a further embodiment the acid is lactic acid, propionic acid, acetic acid, succinic acid, butyric acid or formic acid and the ketone is acetone.

In an advantageous embodiment, the strains according to the present disclosure have the potential to be capable of producing a high amount of lactic acid and/or a salt or an ester thereof. In particular, the strains according to the present disclosure produce a high amount of lactic acid and/or a salt or an ester thereof after 40 h, in particular 60 h of cultivation and/or fermentation time in particular after 90 h of cultivation and/or fermentation time.

The *Caldicellulosiruptor* sp. strains according to the present disclosure have several highly advantageous characteristics needed for the conversion of starch containing biomass/material and/or lignocellulosic biomass material. Thus, these base strains possess all the genetic machinery for the hydrolysis of starch, cellulose and hemicelluloses and for the conversion of both pentose and hexose sugars to various fermentation products such as lactic acid and ethanol. As will be apparent from the below examples, the examination of the complete 16S rDNA sequence showed that the closely related strains may all be related to *Caldicellulosiruptor saccharolyticus* although the 16S rDNA sequences may place them in a separate subspecies or even a different species In a preferred embodiment, the *Caldicellulosiruptor* sp. microorganism is
- a) a microorganism selected from the group consisting of *Caldicellulosiruptor* sp. BluConL70 having the DSMZ Accession number 33496, *Caldicellulosiruptor* sp. BluConL60 having the DSMZ Accession number 33252, *Caldicellulosiruptor* sp. BluCon085 having the DSMZ Accession number 33485 *Caldicellulosiruptor* sp. BluCon052 having the DSMZ Accession number 33470, *Caldicellulosiruptor* sp. BluCon006 having the DSMZ Accession number 33095, *Caldicellulosiruptor* sp. BluCon014 (DSMZ Accession number 33096) and *Caldicellulosiruptor* sp. BluCon016 (DSMZ Accession number 33097,
- b) a microorganism derived from a strain selected from the group consisting of *Caldicellulosiruptor* sp. BluConL70 having the DSMZ Accession number 33496, *Caldicellulosiruptor* sp. BluConL60 having the DSMZ Accession number 33252, *Caldicellulosiruptor* sp. BluCon085 having the DSMZ Accession number 33485 *Caldicellulosiruptor* sp. BluCon052 having the DSMZ Accession number 33470, *Caldicellulosiruptor* sp. BluCon006 having the DSMZ Accession number 33095, *Caldicellulosiruptor* sp. BluCon014 (DSMZ Accession number 33096) and *Caldicellulosiruptor* sp. BluCon016 (DSMZ Accession number 33097 or
- c) a mutant retaining the properties of a strain selected from the group consisting of *Caldicellulosiruptor* sp. BluConL70 having the DSMZ Accession number 33496, *Caldicellulosiruptor* sp. BluConL60 having the DSMZ Accession number 33252, *Caldicellulosiruptor* sp. BluCon085 having the DSMZ Accession number 33485 *Caldicellulosiruptor* sp. BluCon052 having the DSMZ Accession number 33470, *Caldicellulosiruptor* sp. BluCon006 having the DSMZ Accession number 33095, *Caldicellulosiruptor* sp. BluCon014 (DSMZ Accession number 33096) and *Caldicellulosiruptor* sp. BluCon016 (DSMZ Accession number 33097.

All strains and mutant thereof and in table 1 belong to the genus *Caldicellulosiruptor* and are strictly anaerobic, non-sporeforming, non-motile, gram-positive bacteria. Cells are straight rods 0.4-0.5 µm by 2.0-4.0 µm, occurring both singly and in pairs. After 7 days incubation at 72° C. on solid medium with agar and cellulose as substrate both strains form circular milky colonies of 0.5-1 mm in diameter. Clearing zones around the colonies are produced indicating cellulose degradation.

The term "a microorganism" as used herein may refer to only one unicellular organism as well as to numerous single unicellular organisms. For example, the term "a microorganism of the genus *Caldicellulosiruptor*" may refer to one single *Caldicellulosiruptor* bacterial cell of the genus *Caldicellulosiruptor* as well as to multiple bacterial cells of the genus *Caldicellulosiruptor*. The terms "a strain of the genus *Caldicellulosiruptor*" and "a *Caldicellulosiruptor* cell" are used synonymously herein. In general, the term "a microorganism" refers to numerous cells. In particular, said term refers to at least $10^3$ cells, preferably at least $10^4$ cells, at least $10^5$ or at least $10^6$ cells.

As mentioned above cellulosic like lignocellolytic biomass according to the present disclosure can be but is not limited to grass, switch grass, cord grass, rye grass, reed canary grass, mixed prairie grass, miscanthus, Napier grass, sugar-methoding residues, sugarcane bagasse, sugarcane straw, agricultural wastes, rice straw, rice hulls, barley straw, corn cobs, cereal straw, wheat straw, canola straw, oat straw, oat hulls, corn fiber, stover, soybean stover, corn stover, forestry wastes, recycled wood pulp fiber, paper sludge, sawdust, hardwood, softwood, pressmud from sugar beet, cotton stalk, banana leaves, oil palm residues and lignocellulosic biomass material obtained through processing of food plants. In advantageous embodiments, the lignocellulosic biomass material is hardwood and/or softwood, preferably poplar wood. In advantageous embodiments, the lignocellulosic biomass material is a grass or perennial grass, preferably miscanthus.

In advantageous embodiments, the lignocellulosic biomass material is subjected to mechanical, thermochemical, and/or biochemical pretreatment. The lignocellulosic biomass material could be exposed to steam treatment. In further embodiments, the lignocellulosic biomass material is pretreated with mechanical comminution and a subsequent treatment with lactic acid, acetic acid, sulfuric acid or sulfurous acid or their respective salts or anhydrides under heat and pressure with or without a sudden release of pressure. In another embodiment, the lignocellulosic biomass material is pretreated with mechanical comminution and a subsequent treatment with either sodium hydroxide, ammonium hydroxide, calcium hydroxide or potassium hydroxide under heat and pressure with or without a sudden release of pressure.

In advantageous embodiments, the lignocellulosic biomass material is pretreated with mechanical comminution and subsequent exposure to a multi-step combined pretreatment process. Such multi-step combined pretreatment may include a treatment step consisting of cooking in water or steaming of the lignocellulosic biomass material at a temperature of 100-200° C. for a period of time in between 5 and 120 min. Suitable catalysts including but not limited to lactic acid, acetic acid, sulfuric acid, sulfurous acid, sodium hydroxide, ammonium hydroxide, calcium hydroxide or potassium hydroxide or their respective salts or anhydrides may or may not be added to the process. The process may further include a step comprising a liquid-solid separation operation, e.g. filtration, separation, centrifugation or a combination thereof, separating the process fluid containing partially or fully hydrolyzed and solubilized constituents of the lignocellulosic biomass material from the remaining insoluble parts of the lignocellulosic biomass. The process may further include a step comprising washing of the remaining lignocellulosic biomass material. The solid material separated from solubilized biomass constituents may then be treated in a second step with steam under heat and pressure with or without a sudden release of pressure at a temperature of 150-250° C. for a period of time in between 1 and 15 min. In order to increase pretreatement effectiveness, a suitable catalyst including but not limited to lactic acid, acetic acid, sulfuric acid, sulfurous acid, sodium hydroxide, ammonium hydroxide, calcium hydroxide or potassium hydroxide or their respective salts or anhydrides may be added also to the second step.

In advantageous embodiments, the lignocellulosic biomass is milled before converted into biofuels like ethanol and/or carbon-based chemicals like lactic acid. In one embodiment, the lignocellulosic biomass is pretreated biomass from *Populus* sp, preferably pretreated with steam pretreatment or multi-step combined pretreatment. In another embodiment, the lignocellulosic biomass is pretreated biomass from any perennial grass, e.g. *Miscanthus* sp., preferably treated with steam pretreatment or multi-step combined pretreatment.

In advantageous embodiments, the starch-containing biomass is starch-containing plant material, including: tubers, roots, whole grain; and any combination thereof. The starch-containing biomass/material may be obtained from cereals. Suitable starch-containing biomass/material includes corn (maize), wheat, barley, cassava, sorghum, rye, potato, or any combination thereof. Corn is the preferred feedstock, especially when the fermentation product is ethanol. The starch-containing material may also consist of or comprise, e.g., a side stream from starch processing, e.g., C6 carbohydrate containing process streams that may not be suited for production of syrups. Whole stillage typically contains about 10-15 wt-% dry solids. Whole stillage components include fiber, hull, germ, oil and protein components from the starch-containing feedstock as well as non-fermented starch.

In advantageous embodiments the cells, strains, microorganisms may be modified in order to obtain mutants or derivatives with improved characteristics. Thus, in one embodiment there is provided a bacterial strain according to the disclosure, wherein one or more genes have been inserted, deleted or substantially inactivated. The variant or mutant is typically capable of growing in a medium comprising a lignocellulosic biomass material and/or starch containing biomass material.

In another embodiment, there is provided a process for preparing variants or mutants of the microorganisms according to the present disclosure, wherein one or more genes are inserted, deleted or substantially inactivated as described herein.

In some embodiments, one or more additional genes are inserting into the strains according to the present disclosure. Thus, in order to improve the yield of the specific fermentation product, it may be beneficial to insert one or more genes encoding a polysaccharase into the strain according to the invention. Hence, in specific embodiments there is provided a strain and a process according to the invention wherein one or more genes encoding a polysaccharase which is selected from cellulases (such as EC 3.2.1.4); beta-glucanases, including glucan-1,3 beta-glucosidases (exo-1,3 beta-glucanases, such as EC 3.2.1.58), 1,4-beta-cellobiohydrolases (such as EC 3.2.1.91) and endo-1,3(4)-beta-glucanases (such as EC 3.2.1.6); xylanases, including endo-1,4-beta-xylanases (such as EC 3.2.1.8) and xylan 1,4-beta-xylosidases (such as EC 3.2.1.37); pectinases (such as EC 3.2.1.15); alpha-glucuronidases, alpha-L-arabinofuranosidases (such as EC 3.2.1.55), acetylesterases (such as EC 3.1.1.-), acetylxylanesterases (such as EC 3.1.1.72), alpha-amylases (such as EC 3.2.1.1), beta-amylases (such as EC 3.2.1.2), glucoamylases (such as EC 3.2.1.3), pullulanases (such as EC 3.2.1.41), beta-glucanases (such as EC 3.2.1.73), hemicellulases, arabinosidases, mannanases including mannan endo-1,4-beta-mannosidases (such as EC 3.2.1.78) and mannan endo-1,6-alpha-mannosidases (such as EC 3.2.1.101), pectin hydrolases, polygalacturonases (such as EC 3.2.1.15), exopolygalacturonases (such as EC 3.2.1.67) and pectate lyases (such as EC 4.2.2.10), are inserted.

In accordance with the present disclosure, a method of producing a fermentation product comprising culturing a strain according to the invention under suitable conditions is also provided.

The strains according to the disclosure are strictly anaerobic microorganisms, and hence it is preferred that the fermentation product is produced by a fermentation process performed under strictly anaerobic conditions. Additionally, the strain according to invention is an extremely thermophillic microorganism, and therefore the process may perform optimally, when it is operated at temperature in the range of about 40-95 degrees centigrade, such as the range of about 50-90 degrees centigrade, including the range of about 60-85 degrees centigrade, such as the range of about 65-75 degrees centigrade For the production of certain fermentation products, it may be useful to select a specific fermentation process, such as batch fermentation process, including a fed-batch process or a continuous fermentation process. Also, it may be useful to select a fermentation reactor such as a stirred vessel reactor, an immobilized cell reactor, a fluidized bed reactor or a membrane bioreactor.

In accordance with the invention, the method is useful for the production of a wide range of fermentation products including acids, alcohols, ketones and hydrogen. Thus, fermentation products such as ethanol, butanol, propanol, methanol, propanediol, butanediol, lactic acid, propionic acid, acetic acid, succinic acid, butyric acid, formic acid and acetone may be produced in accordance with the disclosure.

For the production of lactic acid, it may be useful to select a specific fermentation process, such as batch fermentation process, including a fed-batch process or a continuous fermentation process. Also, it may be useful to select a fermentation reactor such as a stirred vessel reactor, an immobilized cell reactor, a fluidized bed reactor or a membrane bioreactor.

In accordance with the invention, the method is useful for the production of lactic acid, the enantiomers L-lactic acid and D-lactic acid and the racemic compound D/L-lactic acid.

The fermentation conditions to form lactic acid and/or lactate are known per se and are described in WO 01/27064, WO 99/19290, and WO 98/15517. Accordingly, the temperature may range from 0 to 80° C., while the pH (which decreases upon lactic acid formation) ranges from 3 to 8. A pH below 5 is generally desirable, as part of the lactic acid formed will then be present in its free-acid form instead of in its salt form. Furthermore, at low pH there is less risk of contamination with other microorganisms. Any of the many known types of apparatus may be used for the fermentation according to the present invention.

The microorganism according to the present invention may be used as a biologically pure culture or it may be used with other lactic acid producing microorganisms in mixed culture. Biologically pure cultures are generally easier to optimize but mixed cultures may be able to utilize additional substrates. One may also add enzyme (s) to the fermentation vessel to aid in the degradation of substrates or to enhance lactic acid production. For example, cellulase may be added to degrade cellulose to glucose simultaneously with the fermentation of glucose to lactic acid by microorganisms. Likewise, a hemicellulase may be added to degrade hemicellulose. As mentioned-above, said hydrolyzation (optionally by means of enzymes) may also be conducted prior to fermentation.

The thermophilic *Caldicellulosiruptor* species-containing fermentation broth cultures used in the processes according to the present disclosure are relatively resistant to contamination by other microorganisms.

The thermophilic *Caldicellulosiruptor* species used in the process according to the disclosure may be grown both in so-called chemically defined media and in culture media which contain undefined compounds such as yeast extracts, peptone, tryptone, other meat extracts and complex nitrogen sources. The use of a chemically defined medium is preferred because it results in lactic acid and/or lactate with less impurities.

After fermentation, the lactic acid and/or lactate is separated from the fermentation broth by any of the many conventional techniques known to separate lactic acid and/or lactate from aqueous solutions. Particles of substrate or microorganisms (the biomass) may be removed before separation to enhance separation efficiency. Said separation may be conducted by means of centrifuging, filtration, flocculation, flotation or membrane filtration. This is, for instance, known from WO 01/38283 wherein a continuous process for the preparation of lactic acid by means of fermentation is described. While the discussion of the fermentation in this specification generally refers to a batch process, parts or all of the entire process may be performed continuously. To retain the microorganisms in the fermentor, one may separate solid particles from the fermentation fluids. Alternatively, the microorganisms may be immobilized for retention in the fermentor or to provide easier separation.

After separation of the lactic acid and/or lactate from the fermentation broth, the product may be subjected to one or more purification steps such as extraction, distillation, crystallization, filtration, treatment with activated carbon etcetera. The various residual streams may be recycled, optionally after treatment, to the fermentation vessel or to any previously performed purification step.

The expression "comprise", as used herein, besides its literal meaning also includes and specifically refers to the expressions "consist essentially of" and "consist of". Thus, the expression "comprise" refers to embodiments wherein the subject-matter which "comprises" specifically listed elements does not comprise further elements as well as embodiments wherein the subject-matter which "comprises" specifically listed elements may and/or indeed does encompass further elements. Likewise, the expression "have" is to be understood as the expression "comprise", also including and specifically referring to the expressions "consist essentially of" and "consist of".

The following methods and examples are offered for illustrative purposes only, and are not intended to limit the scope of the present disclosure in any way.

Methods and Examples

In the following examples, materials and methods of the present disclosure are provided including the determination of the properties of the microbial strains according to the present disclosure. It should be understood that these examples are for illustrative purpose only and are not to be construed as limiting this disclosure in any manner.

Description of *Caldicellulosiruptor* sp. Strain BluConL60

*Caldicellulosiruptor* sp strain BluConL60 listed in Table 1 was deposited on Aug. 29, 2019 under the accession number DSM 33252 according to the requirements of the Budapest Treaty, accepted and publicly available at the Deutsche Sammlung von Mikroorganismen und Zellkulturen (DSMZ), Inhoffenstraße 7B, 38124 Braunschweig (DE) by BluCon Biotech GmbH, Nattermannallee 1, 50829 Cologne (DE).

Description of *Caldicellulosiruptor* sp. Strain BluCon006, *Caldicellulosiruptor* sp. Strain BluCon014 and *Caldicellulosiruptor* sp. Strain BluCon016

*Caldicellulosiruptor* sp. BluCon006, *Caldicellulosiruptor* sp. BluCon014 and *Caldicellulosiruptor* sp. BluCon016, which are listed in Table 1, are deposited on Apr. 9, 2019 under the accession numbers DSM 33095, DSM 33096 and DSM 33097 according to the requirements of the Budapest Treaty, accepted and publicly available at the Deutsche Sammlung von Mikroorganismen und Zellkulturen (DSMZ), Inhoffenstraße 7B, 38124 Braunschweig (DE) by BluCon Biotech GmbH, Nattermannallee 1, 50829 Cologne (DE).

Description of *Caldicellulosiruptor* sp. Strain BluCon052 and *Caldicellulosiruptor* sp. Strain BluCon085

*Caldicellulosiruptor* sp. BluCon052 and *Caldicellulosiruptor* sp. BluCon085, which are listed in Table 1, are deposited on Mar. 10, 2020 under the accession numbers DSM 33470 and DSM 33485 according to the requirements of the Budapest Treaty, accepted and publicly available at the Deutsche Sammlung von Mikroorganismen und Zellkulturen (DSMZ), Inhoffenstraße 7B, 38124 Braunschweig (DE) by BluCon Biotech GmbH, Nattermannallee 1, 50829 Cologne (DE).

Description of *Caldicellulosiruptor* sp. strain BluConL70

*Caldicellulosiruptor* sp strain BluConL70 listed in Table 1 was deposited on Mar. 20, 2020 under the accession number DSM 33496 according to the requirements of the Budapest Treaty, accepted and publicly available at the Deutsche Sammlung von Mikroorganismen und Zellkulturen (DSMZ), Inhoffenstraße 7B, 38124 Braunschweig (DE) by BluCon Biotech GmbH, Nattermannallee 1, 50829 Cologne (DE).

Description of *Caldicellulosiruptor* sp. DIB104C

*Caldicellulosiruptor* sp. DIB104C was deposited on Mar. 15, 2012 under the accession number DSM 25774 according to the requirements of the Budapest Treaty, accepted and publicly available at the Deutsche Sammlung von Mikroorganismen und Zellkulturen (DSMZ), Inhoffenstraße 7B, 38124 Braunschweig (DE) by DIREVO Industrial Biotechnology GmbH, Nattermannallee 1, 50829 Cologne (DE).

Description of *Caldicellulosiruptor* sp. DIB101C

*Caldicellulosiruptor* sp. DIB101C was deposited on Sep. 15, 2011 under the accession number DSM 25178 according to the requirements of the Budapest Treaty, accepted and publicly available at the Deutsche Sammlung von Mikroorganismen und Zellkulturen (DSMZ), Inhoffenstraße 7B, 38124 Braunschweig (DE) by DIREVO Industrial Biotechnology GmbH, Nattermannallee 1, 50829 Cologne (DE).

Description of *Caldicellulosiruptor* sp. DIB087C

*Caldicellulosiruptor* sp. DIB087C was deposited on Mar. 15, 2012 under the accession number DSM 25772 according to the requirements of the Budapest Treaty, accepted and publicly available at the Deutsche Sammlung von Mikroorganismen und Zellkulturen (DSMZ), Inhoffenstraße 7B, 38124 Braunschweig (DE) by DIREVO Industrial Biotechnology GmbH, Nattermannallee 1, 50829 Cologne (DE).

Description of *Caldicellulosiruptor saccharolyticus* DSM 8903

*Caldicellulosiruptor saccharolyticus* DSM 8903 originates from Deutsche Sammlung von Mikroorganismen und Zellkulturen (DSMZ), Inhoffenstraße 7B, 38124 Braunschweig (DE).

Reference literature: Rainey et al., 1994. Description of *Caldicellulosiruptor saccharolyticus* gen. nov., sp. nov.: an obligately anaerobic, extremely thermophilic, cellulolytic bacterium. FEMS Microbiol. Lett. 120: 263-266.

Description of *Caldicellulosiruptor bescii* DSM 6725
*Caldicellulosiruptor bescii* DSM 6725 originates from Deutsche Sammlung von Mikroorganismen und Zellkulturen (DSMZ), Inhoffenstraße 7B, 38124 Braunschweig (DE).

REFERENCE LITERATURE a) Svetlichnyi et al., 1990. *"Anaerocellum thermophilum* gen. nov. sp. nov. an extremely thermophilic cellulolytic *eubacterium* isolated from hot-springs in the valley of geysers". Mikrobiologiâ. 59: 598-604
b) Yang et al., 2010. Classification of '*Anaerocellum thermophilum*' strain DSM 6725 as *Caldicellulosiruptor bescii* sp. nov. International Journal of Systematic and Evolutionary Microbiology. 60. 9. 2011-5.

Example 1: Cultivation of Seed Culture A

All procedures for enrichment and isolation of the strains listed in Table 1 employed anaerobic technique for strictly anaerobic bacteria (Hungate 1969). The strains listed in Table 1 were cultivated at 70° C. with crystalline cellulose as substrate in seed medium A. The cells are cultured under strictly anaerobic conditions applying the following basic medium:

| Seed medium A | | |
|---|---|---|
| Crystalline cellulose (Avicel pH 101) | 10 | g |
| $NH_4Cl$ | 1.0 | g |
| NaCl | 0.5 | g |
| $MgSO_4 \times 7H_2O$ | 0.3 | g |
| $CaCl_2 \times 2H_2O$ | 0.05 | g |
| $NaHCO_3$ | 0.5 | g |
| $K_2HPO4$ | 1.5 | g |
| $KH_2PO_4$ | 3.0 | g |
| Yeast extract (BD) | 0.5 | g |
| Trace elements stock solution | 0.5 | ml |
| Resazurin, Na-salt | 0.25 | mg |
| L-cysteine | 0.5 | g |
| Distilled water | 1000 | ml |

| Trace elements stock solution | | |
|---|---|---|
| $NiCl_2 \times 6H_2O$ | 2 | g |
| $FeSO_4 \times 7H_2O$ | 1 | g |
| $NH_4Fe(III)$ citrate, 18% Fe | 10 | g |
| $MnSO_4 \times H_2O$ | 5 | g |
| $CoCl_2 \times 6H_2O$ | 1 | g |
| $ZnSO_4 \times 7H_2O$ | 1 | g |
| $CuSO_4 \times 5H_2O$ | 0.1 | g |
| $H_3BO_3$ | 0.1 | g |
| $Na_2MoO_4 \times 2H_2O$ | 0.1 | g |
| $Na_2SeO_3$ | 0.2 | g |
| $Na_2WoO_4 \times 2H_2O$ | 0.13 | g |
| Distilled water | 1000 | ml |

All ingredients except L-cysteine were dissolved in deionized water and the medium was flushed with nitrogen gas (purity 99.999%) for 20 min at room temperature and the pH-value was adjusted to 7.0 at room temperature with 5 M NaOH. Then a sterile stock solution of L-cysteine, which had been filtered into a nitrogen containing serum flasks, was added to the medium. The medium was then dispensed into serum flasks under nitrogen atmosphere and the vessels are tightly sealed. After autoclaving at 121° C. for 20 min pH-value should be in between 7.0 and 7.2.

Subsequent to autoclaving, cultures were inoculated by injection of the seed culture A through the seal septum and inoculated in an incubator at 70° C. for 24 to 48 hours.

Example 2: HPLC

Sugars and fermentation products were quantified by HPLC-RI using a Prominence LC-20AD HPLC (company Shimadzu) fitted with a Rezex ROA Organic Acid H+ (Phenomenex). The analytes were separated isocratically with 2.5 mM $H_2SO_4$ and at 65° C.

Example 3: Fermentation

Batch experiments with the strains BluCon006, BluCon014 and BluCon016, were performed by cultivation on the following fermentation medium with addition of 80 g/L of microcrystalline cellulose:

| Fermentation medium | | |
|---|---|---|
| $(NH_4)_2HPO_4$ | 0.5 to 1.0 | g |
| $(NH_4)_2SO_4$ | 2.0 to 5.0 | g |
| NaCl | 0.1 to 0.5 | g |
| $MgSO_4 \times 7 H_2O$ | 0.2 to 0.8 | g |
| $CaCl_2 \times 2 H_2O$ | 0.05 to 0.3 | g |
| $KH_2PO_4$ | 0.2 to 0.5 | g |
| Yeast extract | 1.0 to 6.0 | g |
| Meat extract | 2.0 to 10.0 | g |
| Corn steep liquor | 1.0 to 5.0 | g |
| Peptone | 5.0 to 10 | g |
| Trace elements stock solution | 0.5 to 1.0 | ml |
| Resazurin, Na-salt | 0.25 | mg |
| L-cysteine | 0.5 | g |
| Distilled water | 1000 | ml |

All ingredients are dissolved in deionized water and added into 2 L fermentation vessels with stirrers and pH and temperature control (company BBI). The pH-value should be in between 6.8 and 7.0 (adjusted with NaOH or HCL).

After autoclaving at 121° C. for 20 min the medium is flushed with nitrogen gas (purity 99,999%) for 20 mi at room temperature to remove excess oxygen before L-cysteine is added as described above.

Temperature is controlled to 62 to 75° C. and the pH-value is controlled to 5.8 to 7.2 throughout the fermentation by SM NaOH. The fermentation is started by addition of a seed culture prepared as described in example 1. The results are presented in table 2.

TABLE 2

Lactic acid, acetic acid and ethanol from microcrystalline cellulose at different cultivation times.

| Strain | Cultivation time [h] | Lactic acid [g/l] | Acetic acid [g/]) | Ethanol [g/l] |
|---|---|---|---|---|
| DIB104C | 17.8 | 6.2 | 0.4 | 0.3 |
| | 41.2 | 18.3 | 0.9 | 0.7 |
| | 64.9 | 17.4 | 2.6 | 0.8 |
| BluCon006 | 17.3 | 0.2 | 0.0 | 0.1 |
| | 40.7 | 7.2 | 0.2 | 0.2 |
| | 62.5 | 27.8 | 0.1 | 0.5 |
| | 91.5 | 31.1 | 0.3 | 0.6 |
| BluCon014 | 17.8 | 8.5 | 0.1 | 0.3 |
| | 41.1 | 22.5 | 0.1 | 0.5 |
| | 63.4 | 26.3 | 0.1 | 0.6 |
| | 91.9 | 28.8 | 0.2 | 0.7 |

TABLE 2-continued

Lactic acid, acetic acid and ethanol from microcrystalline cellulose at different cultivation times.

| Strain | Cultivation time [h] | Lactic acid [g/l] | Acetic acid [g/l] | Ethanol [g/l] |
|---|---|---|---|---|
| BluCon016 | 18.2 | 8.9 | 0.1 | 0.3 |
|  | 41.4 | 22.1 | 0.1 | 0.5 |
|  | 63.8 | 24.3 | 0.1 | 0.6 |
|  | 92.2 | 26.0 | 0.2 | 0.7 |

The results of the HPLC analysis as described in example 2 show that BluCon006, BluCon014 and BluCon016 produce higher lactic acid concentrations and lower acetic acid and ethanol concentrations in the fermentation compared to the reference strain, DIB104C (see Table 2).

Example 3a: Fermentation with Microcrystalline Cellulose and NaOH as pH Regulator Batch experiments with the strains BluConL60, BluCon006, BluCon014 and BluCon016 were performed by cultivation on the following fermentation medium with addition of 80 g/L of microcrystalline cellulose:

| Fermentation medium A | | |
|---|---|---|
| Microcrystalline cellulose (Avicel PH-101) | 80 | g |
| $(NH_4)_2HPO_4$ | 0.5 to 1.0 | g |
| $(NH_4)_2SO_4$ | 2.0 to 5.0 | g |
| NaCl | 0.1 to 0.5 | g |
| $MgSO_4 \times 7\,H_2O$ | 0.2 to 0.8 | g |
| $CaCl_2 \times 2\,H_2O$ | 0.05 to 0.3 | g |
| $KH_2PO_4$ | 0.2 to 0.5 | g |
| Yeast extract | 1.0 to 6.0 | g |
| Meat extract | 2.0 to 10.0 | g |
| Corn steep liquor | 1.0 to 5.0 | g |
| Peptone | 5.0 to 10 | g |
| Trace elements stock solution | 0.5 to 1.0 | ml |
| Resazurin, Na-salt | 0.25 | mg |
| L-cysteine | 0.5 | g |
| Distilled water | 1000 | ml |

All ingredients except for the microcrystalline cellulose were dissolved in deionized water and added into 2 L fermentation vessels with stirrers and pH and temperature control (company BBI). The pH-value should be in between 6.8 and 7.0 (adjusted with NaOH or HCL).

After autoclaving at 121° C. for 20 min the medium was flushed with nitrogen gas (purity 99.999%) for 20 min at room temperature to remove excess oxygen before L-cysteine was added as described above.

Temperature was controlled to 62 to 75° C. and the pH-value was controlled from 5.8 to 7.2 throughout the fermentation by 5 M NaOH. The fermentation was started by addition of seed culture A prepared as described in example 1. Samples were taken and sugars and fermentation products were quantified by HPLC analysis as described in example 2. The results are presented in Table 3.

TABLE 3

Lactic acid from microcrystalline cellulose by BluConL60, BluCon006, BluCon014 and BluCon016 compared to DIB104C at different cultivation times.

| Strain | Cultivation time [h] | Lactic acid [g/l] |
|---|---|---|
| BluConL60 | 14.7 | 1.8 |
|  | 40.3 | 18.7 |
|  | 68.8 | 35.0 |
|  | 92.8 | 36.7 |
| DIB104C | 17.8 | 6.2 |
|  | 41.2 | 18.3 |
|  | 64.9 | 17.4 |
| BluCon006 | 17.3 | 0.2 |
|  | 40.7 | 7.2 |
|  | 62.5 | 27.8 |
|  | 91.5 | 31.1 |
| BluCon014 | 17.8 | 8.5 |
|  | 41.1 | 22.5 |
|  | 63.4 | 26.3 |
|  | 91.9 | 28.8 |
| BluCon016 | 18.2 | 8.9 |
|  | 41.4 | 22.1 |
|  | 63.8 | 24.3 |
|  | 92.2 | 26.0 |

The results of the HPLC analysis as described in example 2 show that BluConL60, BluCon006, BluCon014 BluCon016 and DIB104C produces high amount of lactic acid concentrations with crystalline cellulose compared to the reference strain DIB104C, in particular after a time of 60 h (see Table 3).

Example 3b: Fermentation with Microcrystalline Cellulose and $Ca(OH)_2$ as pH Regulator Batch experiments with the strains listed in Table 1 were performed by cultivation on the following fermentation medium with addition of 80 to 200 g/L of microcrystalline cellulose:

| Fermentation medium A | | |
|---|---|---|
| Microcrystalline cellulose (Avicel PH-101) | 50 to 200 | g |
| $(NH_4)_2HPO_4$ | 0.5 to 1.0 | g |
| $(NH_4)_2SO_4$ | 2.0 to 5.0 | g |
| NaCl | 0 to 0.5 | g |
| $NaCH_3COO \times 3\,H_2O$ | 0 to 0.5 | g |
| $MgSO_4 \times 7\,H_2O$ | 0.2 to 0.8 | 8 |
| $CaCl_2 \times 2\,H_2O$ | 0 to 0.3 | g |
| $Ca(CH_3COO)_2 \times H_2O$ | 0 to 0.3 | g |
| $KH_2PO_4$ | 0.2 to 0.5 | g |
| Yeast extract | 1.0 to 6.0 | g |
| Meat extract | 2.0 to 10.0 | g |
| Corn steep liquor | 1.0 to 5.0 | g |
| Peptone | 5.0 to 10 | g |
| Trace elements stock solution | 0.5 to 1.0 | ml |
| Resazurin, Na-salt | 0.25 | mg |
| L-cysteine | 0.5 | g |
| Distilled water | 1000 | ml |

All ingredients except for the micro crystalline cellulose were dissolved in deionized water and added into 2 L fermentation vessels with stirrers and pH and temperature control (company bbi-biotech, Berlin). The pH-value should be in between 5.8 and 7.2 (adjusted with $Ca(OH)_2$).

After autoclaving at 121° C. for 20 min the medium was flushed with nitrogen gas (purity 99.999%) for 20 min at room temperature to remove excess oxygen before L-cysteine was added as described above.

Temperature was controlled to 62 to 75° C. and the pH-value was controlled from 5.8 to 7.2 throughout the fermentation by 1 to 3 M Ca(OH)$_2$. The fermentation was started by addition of seed culture A prepared as described in example 1. Samples were taken and sugars and fermentation products were quantified by HPLC analysis as described in example 2. The results are presented in Table 4 (a to k) and in FIG. 1 and FIG. 2.

Table 4 (a to k). Lactic acid from microcrystalline cellulose by BluConL70 (Table 4a), BluConL60 (Table 4b and Table 4g), BluCon085 (Table 4c), BluCon052 (Table 4d), BluCon006 (Table 4h), BluCon014 (Table 4i) and BluCon016 (Table 4e, Table 4j) compared to DIB104C (Table 4f and Table 4k) at different cultivation times.

TABLE 4a

Results of BluConL70.

| Strain | Cultivation time [h] | Lactic acid [g/l] |
|---|---|---|
| BluConL70 | 19.83 | 6.6 |
|  | 25.08 | 11.2 |
|  | 44.17 | 26.8 |
|  | 69.58 | 43.9 |
|  | 94.25 | 56.1 |
|  | 115.58 | 62.2 |
|  | 139.92 | 65.4 |
|  | 163.58 | 66.3 |
|  | 187.58 | 66.1 |
|  | 211.67 | 67.0 |

TABLE 4b

Results of BluConL60.

| Strain | Cultivation time [h] | Lactic acid [g/l] |
|---|---|---|
| BluConL60 | 0.17 | 0.1 |
|  | 19.33 | 0.9 |
|  | 43.42 | 21.1 |
|  | 70.50 | 36.5 |
|  | 95.08 | 46.0 |
|  | 115.67 | 50.1 |
|  | 139.08 | 53.5 |
|  | 163.75 | 55.4 |
|  | 187.17 | 55.9 |

TABLE 4c

Results of BluCon085

| Strain | Cultivation time [h] | Lactic acid [g/l] |
|---|---|---|
| BluCon085 | 0.25 | 0.1 |
|  | 18.92 | 0.6 |
|  | 42.92 | 6.5 |
|  | 69.92 | 18.1 |
|  | 94.67 | 27.2 |
|  | 115.25 | 30.9 |
|  | 138.67 | 34.0 |
|  | 163.33 | 39.8 |
|  | 190.17 | 47.1 |
|  | 211.67 | 51.5 |
|  | 234.25 | 57.2 |
|  | 263.92 | 60.5 |
|  | 284.17 | 63.4 |
|  | 307.00 | 62.8 |

TABLE 4d

Results of BluCon052.

| Strain | Cultivation time [h] | Lactic acid [g/l] |
|---|---|---|
| BluCon052 | 1.00 | 0.1 |
|  | 21.83 | 4.2 |
|  | 47.58 | 23.3 |
|  | 67.92 | 27.9 |
|  | 91.50 | 31.3 |
|  | 116.67 | 33.8 |
|  | 143.00 | 43.1 |
|  | 164.00 | 45.4 |
|  | 186.92 | 50.0 |
|  | 215.17 | 53.2 |
|  | 236.17 | 54.4 |

TABLE 4e

Results of BluCon016.

| Strain | Cultivation time [h] | Lactic acid [g/l] |
|---|---|---|
| BluCon016 | 0.25 | 0.2 |
|  | 16.92 | 6.4 |
|  | 21.00 | 11.3 |
|  | 24.75 | 17.3 |
|  | 41.17 | 26.3 |
|  | 45.00 | 27.5 |
|  | 48.92 | 28.4 |
|  | 65.83 | 30.0 |

TABLE 4f

Results of DIB104C.

| Strain | Cultivation time [h] | Lactic acid [g/l] |
|---|---|---|
| DIB104C | 0.17 | 0.1 |
|  | 16.75 | 3.7 |
|  | 20.83 | 6.3 |
|  | 24.67 | 9.1 |
|  | 41.08 | 16.8 |
|  | 44.92 | 16.7 |
|  | 48.83 | 16.9 |
|  | 65.75 | 17.3 |

TABLE 4g

Results of BluConL60.

| Strain | Cultivation time [h] | Lactic acid [g/l] |
|---|---|---|
| BluConL60 | 20.50 | 2.3 |
|  | 92.00 | 43.6 |
|  | 116.58 | 51.2 |
|  | 140.50 | 56.4 |
|  | 188.67 | 57.4 |

TABLE 4h

Results of BluCon006.

| Strain | Cultivation time [h] | Lactic acid [g/l] |
|---|---|---|
| BluCon006 | 20.92 | 2.5 |
|  | 92.25 | 26.0 |
|  | 116.67 | 28.6 |
|  | 140.58 | 30.9 |
|  | 188.33 | 35.5 |

TABLE 4i

Results of BluCon014.

| Strain | Cultivation time [h] | Lactic acid [g/l] |
|---|---|---|
| BluCon014 | 21.25 | 6.9 |
| | 92.50 | 29.3 |
| | 116.00 | 29.5 |
| | 140.17 | 29.6 |
| | 188.50 | 31.5 |

TABLE 4j

Results of BluCon016.

| Strain | Cultivation time [h] | Lactic acid [g/l] |
|---|---|---|
| BluCon016 | 21.50 | 10.4 |
| | 92.83 | 29.5 |
| | 116.42 | 31.3 |
| | 140.17 | 34.0 |
| | 188.42 | 36.9 |

TABLE 4k

Results of DIB104C.

| Straits | Cultivation time [h] | Lactic acid [g/l] |
|---|---|---|
| DIB104C | 20.50 | 7.0 |
| | 45.58 | 15.8 |
| | 68.42 | 17.0 |
| | 91.58 | 17.6 |

The results of the HPLC analysis as described in example 2 show that BluConL70, BluCon085, BluCon052, BluConL60, BluCon016, BluCon014 and BluCon006 produce higher lactic acid concentrations in same time intervals in the fermentation with crystalline cellulose compared to the reference strain DIB104C (see Table 4 a to k).

Example 4: Cultivation of Seed Culture B

All procedures for enrichment and isolation of the strains listed in Table 1 employed anaerobic technique for strictly anaerobic bacteria (Hungate 1969). The strains listed in Table 1 were cultivated at 70° C. with filter paper (i.e. cellulose) as substrate in seed medium B. The cells were cultured under strictly anaerobic conditions applying the following basic medium:

| Seed medium B | | |
|---|---|---|
| Filter paper Whatman#1 (of the size of 1 × 6 cm (approx. 50 mg) was added) | Approx.. 5.0 | g |
| D-glucose, water free | 0.5 | g |
| NH$_4$Cl | 1.0 | g |
| NaCl | 0.5 | g |
| MgSO$_4$ × 7 H$_2$O | 0.3 | g |
| CaCl$_2$ × 2 H$_2$O | 0.05 | g |
| NaHCO$_3$ | 0.5 | g |
| K$_2$HPO$_4$ | 1.5 | g |
| KH$_2$PO$_4$ | 3.0 | g |
| Yeast extract (BD) | 0.5 | g |
| Trace elements stock solution | 0.5 | ml |
| Resazurin, Na-salt | 0.25 | mg |
| L-cysteine | 0.5 | g |
| Distilled water | 1000 | ml |

| Trace elements stock solution | | |
|---|---|---|
| NiCl$_2$ × 6H$_2$O | 2 | g |
| FeSO$_4$ × 7H$_2$O | 1 | g |
| NH$_4$Fe(III) citrate, 18% Fe | 10 | g |
| MnSO$_4$ × H$_2$O | 5 | g |
| CoCl$_2$ × 6H$_2$O | 1 | g |
| ZnSO$_4$ × 7H$_2$O | 1 | g |
| CuSO$_4$ × 5H$_2$O | 0.1 | g |
| H$_3$BO$_3$ | 0.1 | g |
| Na$_2$MoO$_4$ × 2H$_2$O | 0.1 | g |
| Na$_2$SeO$_3$ | 0.2 | g |
| Na$_2$WoO$_4$ × 2H$_2$O | 0.13 | g |
| Distilled water | 1000 | ml |
| Add 0.5 ml of the trace elements stock solution to 1 liter of the medium | | |

Cultivation was performed in 16 ml total volume in Hungate tubes, with butyl rubber stoppers and screw caps. Into each tube one strip of filter paper, Whatman #1 of the size of 1×6 cm (approx. 50 mg) had been added. The tubes containing the filter paper were flushed with nitrogen gas (purity 99.999%); closed with rubber stoppers and incubated for 60 minutes to remove oxygen from paper.

In seed medium B all ingredients except L-cysteine are dissolved in deionized water and the medium was flushed with nitrogen gas (purity 99.999%) for 20 min at room temperature and the pH-value was adjusted to 7.0 at room temperature with 5 M NaOH. Then a sterile stock solution of L-cysteine, which had been filtered into a nitrogen containing serum flasks, was added to the medium. The medium was then dispensed into serum flasks under nitrogen atmosphere and the vessels were tightly sealed. After autoclaving at 121° C. for 20 min pH-value should be in between 7.0 and 7.2. Subsequent to autoclaving, cultures were inoculated by injection of the seed culture B through the seal septum and inoculated in an incubator at 70° C. for 24 to 48 hours.

Example 5: Fermentation with Microcrystalline Cellulose in Serum Bottles

Batch experiments with strains listed in Table 1 were performed by cultivation on the following fermentation medium with addition of 90 and 120 g/L of microcrystalline cellulose (Avicel pH 101) and 10 to 100 g/l CaCO$_3$:

| Fermentation medium B | | |
|---|---|---|
| CaCO$_3$ | 10 to 100 | g |
| microcrystalline cellulose (Avicel pH 101) | 90/120 | g |
| (NH$_4$)$_2$HPO$_4$ | 0.5 to 1.0 | g |
| (NH$_4$)$_2$SO$_4$ | 2.0 to 5.0 | g |
| NaCl | 0.1 to 0.5 | g |
| MgSO$_4$ × 7 H$_2$O | 0.2 to 0.8 | g |
| CaCl$_2$ × 2 H$_2$O | 0.05 to 0.5 | g |
| KH$_2$PO$_4$ | 0.2 to 0.5 | g |
| Yeast extract | 1.0 to 6.0 | g |
| Meat extract | 2.0 to 10.0 | g |
| Corn steep liquor | 1.0 to 5.0 | g |
| Peptone | 5.0 to 10 | g |
| Trace elements stock solution | 0.5 to 1.0 | ml |
| Vitamin stock solution | 1.0 to 4.0 | ml |
| Resazurin, Na-salt | 0.25 | mg |
| L-cysteine | 0.5 | g |
| Distilled water | 1000 | ml |

| Vitamin stock solution | | |
|---|---|---|
| Nicotinic acid | 1000 | mg |
| Cyanocobalamin (B12) | 125 | mg |
| p-Aminobenzoic acid (4-aminobenzoic acid) | 125 | mg |
| Calcium D-pantothenate | 125 | mg |
| Thiamine-HCl | 125 | mg |
| Riboflavin (B2) | 125 | mg |
| Lipoic acid | 125 | mg |
| Folic acid | 50 | mg |
| Biotin (vitamin H) | 50 | mg |
| Pyridoxin-HCl (B6) | 50 | mg |
| Distilled water | 1000 | ml |

Cultivations were performed in 110 ml serum bottles closed with butyl rubber stoppers and aluminum crimp seals. All ingredients except L-cysteine were dissolved in deionized water and the medium was flushed with nitrogen gas (purity 99.999%) for 20 min at room temperature. Then a sterile stock solution of L-cysteine, which had been filtered into a nitrogen containing serum flasks, was added to the medium. The medium was then dispensed into serum flasks under nitrogen atmosphere and the vessels were tightly sealed. After autoclaving at 121° C. for 20 min pH-value should be in between 7.1 and 7.3. Duplicate fermentations were started by addition of seed culture B prepared as described in example 4. The cultures were incubated at 72° C. for four seven days. Samples were taken and sugars and fermentation products were quantified by HPLC analysis as described in example 2. The results are presented in Table 5.

TABLE 5

Lactic acid (averages of two fermentations and deviations from the averages) from microcrystalline cellulose (90 g/l and 120 g/l) by BluConL70, BluCon085, BluCon052, BluConL60, BluCon006, BluCon014 and BluCon016 compared to DIB104C, DIB 087C, DIB 101C, *Caldicellulosiruptor bescii* DSM 6725 and *Caldicellulosiruptor saccharolyticus* DSM 8903 after even days cultivation.

| s | Lactic acid [g/l] after seven days from 90 g/l Avicel pH101 | Lactic acid [g/l] after seven days from 120 g/l Avicel pH101 |
|---|---|---|
| BluConL70 | — | 40.7 ± 0.3 |
| BluCon085 | 36.1 ± 0.4 | — |
| BluCon052 | 24.8 ± 0.6 | — |
| BluConL60 | 35.8 ± 0.8 | 39.9 ± 1.0 |
| BluCon016 | 22.8 ± 0.2 | — |
| BluCon014 | 23.0 ± 0.4 | — |
| BluCon006 | 22.6 ± 0.2 | — |
| DIB104C | 16.3 ± 0.2 | 16.7 ± 0.3 |
| DIB 087C | — | 2.1 ± 0.1 |
| DIB 101C | — | 5.6 ± 0.2 |
| *Caldicellulosiruptor bescii* DSM 6725 | — | 3.2 ± 0.1 |
| *Caldicellulosiruptor saccharolyticus* DSM 8903 | — | 7.5 ± 0.2 |

The results of the HPLC analysis as described in example 2 show that BluConL70, BluCon085, BluCon052, BluConL60, BluCon016, BluCon014 and BluCon006 produce higher lactic acid concentrations from microcrystalline cellulose compared to the reference strains DIB104C, DIB 087C, DIB 101C, *Caldicellulosiruptor bescii* DSM 6725 and *Caldicellulosiruptor saccharolyticus* DSM 8903 (see Table 5).

This makes the fermentative production of lactic acid from cellulosic substrates with BluConL70, BluCon085, BluCon052, BluConL60, BluCon016, BluCon014 and BluCon006 commercially more attractive compared to the process with DIB104C Example 6: Fermentation with Starch (Soluble)

Batch experiments with the strains BluConL60, BluCon006, BluCon014 BluCon016 and DIB104C were performed by cultivation on the following fermentation medium with addition of 90 g/L of starch (soluble) and 10 to 100 g/l $CaCO_3$:

| Fermentation medium B | | |
|---|---|---|
| $CaCO_3$ | 10 to 100 | g |
| Starch (soluble) | 90 | g |
| $(NH_4)_2HPO_4$ | 0.5 to 1.0 | g |
| $(NH_4)_2SO_4$ | 2.0 to 5.0 | g |
| NaCl | 0.1 to 0.5 | g |
| $MgSO_4 \times 7\ H_2O$ | 0.2 to 0.8 | g |
| $CaCl_2 \times 2\ H_2O$ | 0.05 to 0.5 | g |
| $KH_2PO_4$ | 0.2 to 0.5 | g |
| Yeast extract | 1.0 to 6.0 | g |
| Meat extract | 2.0 to 10.0 | g |
| Corn steep liquor | 1.0 to 5.0 | g |
| Peptone | 5.0 to 10 | g |
| Trace elements stock solution | 0.5 to 1.0 | ml |
| Vitamin stock solution | 1.0 to 4.0 | ml |
| Resazurin, Na-salt | 0.25 | mg |
| L-cysteine | 0.5 | g |
| Distilled water | 1000 | ml |

| Vitamin stock solution | | |
|---|---|---|
| Nicotinic acid | 1000 | mg |
| Cyanocobalamin (B12) | 125 | mg |
| p-Aminobenzoic acid (4-aminobenzoic acid) | 125 | mg |
| Calcium D-pantothenate | 125 | mg |
| Thiamine-HCl | 125 | mg |
| Riboflavin (B2) | 125 | mg |
| Lipoic acid | 125 | mg |
| Folic acid | 50 | mg |
| Biotin (vitamin H) | 50 | mg |
| Pyridoxin-HCl (B6) | 50 | mg |
| Distilled water | 1000 | ml |

Cultivation was performed in 100 ml serum bottles closed with butyl rubber stoppers and aluminum crimp seals. All ingredients except L-cysteine were dissolved in deionized water and the medium was flushed with nitrogen gas (purity 99.999%) for 20 min at room temperature. Then a sterile stock solution of L-cysteine, which had been filtered into a nitrogen containing serum flasks, was added to the medium. The medium was then dispensed into serum flasks under nitrogen atmosphere and the vessels were tightly sealed. After autoclaving at 121° C. for 20 min pH-value should be in between 7.1 and 7.3. Duplicate fermentations were started by addition of seed culture B prepared as described in example 4. The cultures were incubated at 72° C. for four days. Samples were taken and sugars and fermentation products were quantified by HPLC analysis as described in example 2. The results are presented in Table 6.

TABLE 6

Lactic acid (average of two fermentations) from soluble starch by strains BluConL60, BluCon006, BluCon014 and BluCon016 compared to DIB1040 after 4 days cultivation.

| Strain | Lactic acid [g/l] |
|---|---|
| BluConL60 | 43.8 ± 1.2 |
| DIB104C | 13.0 ± 0.3 |
| BluCon006 | 29.1 ± 0.4 |
| BluCon014 | 23.1 ± 0.5 |
| BluCon016 | 22.9 ± 0.6 |

The results of the HPLC analysis as described in example 2 show that the strains BluConL60, BluCon006, BluCon014 and BluCon016 produce higher lactic acid concentrations in the fermentation from starch compared to the reference strain DIB104C, (see Table 6).

Example 7: Fermentation with Starch (Soluble) in Serum Bottles

Batch experiments with strains listed in Table 1 were performed by cultivation on the following fermentation medium with addition of 90 g/L of starch (soluble) and 10 to 100 g/l $CaCO_3$:

| Fermentation medium B | | |
|---|---|---|
| $CaCO_3$ | 10 to 100 | g |
| Starch (soluble) | 90 | g |
| $(NH_4)_2HPO_4$ | 0.5 to 1.0 | g |
| $(NH_4)_2SO_4$ | 2.0 to 5.0 | g |
| NaCl | 0.1 to 0.5 | g |
| $MgSO_4 \times 7\ H_2O$ | 0.2 to 0.8 | g |
| $CaCl_2 \times 2\ H_2O$ | 0.05 to 0.5 | g |
| $KH_2PO_4$ | 0.2 to 0.5 | g |
| Yeast extract | 1.0 to 6.0 | g |
| Meat extract | 2.0 to 10.0 | g |
| Corn steep liquor | 1.0 to 5.0 | g |
| Peptone | 5.0 to 10 | g |
| Trace elements stock solution | 0.5 to 1.0 | ml |
| Vitamin stock solution | 1.0 to 4.0 | ml |
| Resazurin, Na-salt | 0.25 | mg |
| L-cysteine | 0.5 | g |
| Distilled water | 1000 | ml |

| Vitamin stock solution | | |
|---|---|---|
| Nicotinic acid | 1000 | mg |
| Cyanocobalamin (B12) | 125 | mg |
| p-Aminobenzoic acid (4-aminobenzoic acid) | 125 | mg |
| Calcium D-pantothenate | 125 | mg |
| Thiamine-HCl | 125 | mg |
| Riboflavin (B2) | 125 | mg |
| Lipoic acid | 125 | mg |
| Folic acid | 50 | mg |
| Biotin (vitamin H) | 50 | mg |
| Pyridoxin-HCl (B6) | 50 | mg |
| Distilled water | 1000 | ml |

Cultivations were performed in 110 ml serum bottles closed with butyl rubber stoppers and aluminum crimp seals. All ingredients except L-cysteine were dissolved in deionized water and the medium was flushed with nitrogen gas (purity 99.999%) for 20 min at room temperature. Then a sterile stock solution of L-cysteine, which had been filtered into a nitrogen containing serum flasks, was added to the medium. The medium was then dispensed into serum flasks under nitrogen atmosphere and the vessels were tightly sealed. After autoclaving at 121° C. for 20 min pH-value should be in between 7.1 and 7.3. Duplicate fermentations were started by addition of seed culture B prepared as described in example 4. The cultures were incubated at 72° C. for four days or for seven days. Samples were taken and sugars and fermentation products were quantified by HPLC analysis as described in example 2. The results are presented in Table 7.

TABLE 7

Lactic acid (averages of two fermentations and deviations from the averages) from soluble starch by BluConL70, BluCon085, BluCon052, BluConL60, BluCon006, BluCon014 and BluCon016 compared to DIB104C, DIB 087C, DIB 101C, Caldicellulosiruptor bescii DSM 6725 and Caldicellulosiruptor saccharolyticus DSM 8903 after four and seven days cultivation.

| Strain | Lactic acid [g/l] after four days | Lactic acid [g/l] after seven days |
|---|---|---|
| BluConL70 | — | 42.2 ± 0.9 |
| BluCon085 | 33.8 ± 0.0 | — |
| BluCon052 | 40.1 ± 0.3 | — |
| BluConL60 | 43.8 ± 1.2 | 43.5 ± 0.3 |
| BluCon016 | 22.9 ± 0.6 | — |
| BluCon014 | 23.1 ± 0.5 | — |
| BluCon006 | 29.1 ± 0.4 | — |
| DIB104C | 13.0 ± 0.3 | 17.4 ± 0.1 |
| DIB 087C | — | 9.5 ± 0.3 |
| DIB 101C | — | 9.8 ± 0.4 |
| Caldicellulosiruptor bescii DSM 6725 | — | 5.1 ± 0.4 |
| Caldicellulosiruptor saccharolyticus DSM 8903 | — | 8.4 ± 0.2 |

The results of the HPLC analysis as described in example 2 show that BluConL70, BluCon085, BluCon052, BluConL60, BluCon016, BluCon014 and BluCon006 produce higher lactic acid concentrations from starch compared to the reference strains DIB104C, DIB 087C, DIB 101C, Caldicellulosiruptor bescii DSM 6725 and Caldicellulosiruptor saccharolyticus DSM 8903 (see Table 7).

This makes the fermentative production of lactic acid from starchy substrates with BluConL70, BluCon085, BluCon052, BluConL60, BluCon016, BluCon014 and BluCon006 commercially more attractive compared to the process with DIB104C, DIB 087C, DIB 101C, Caldicellulosiruptor bescii DSM 6725 and Caldicellulosiruptor saccharolyticus DSM 8903.

Example 8: Lactate Biosensor

L-lactic acid concentration of the samples were quantified by the lactate biosensor LaboTRACE compact (company TRACE Analytics GmbH, Braunschweig, Germany) according to the instructions of the company.

Example 9: Fermentation with Unmodified Starch (Pure Potato Starch)

Batch experiments with strain BluConL60 were performed in cultivations in the following fermentation medium.

| Fermentation medium | | |
|---|---|---|
| $CaCO_3$ | 10 to 100 | g |
| Unmodified starch (pure potato starch) | 50 | g |

| Fermentation medium | | |
|---|---|---|
| (NH$_4$)$_2$HPO$_4$ | 0.5 to 1.0 | g |
| (NH$_4$)$_2$SO$_4$ | 2.0 to 5.0 | g |
| NaCl | 0.1 to 0.5 | g |
| MgSO$_4$ x 7 H$_2$O | 0.2 to 0.8 | g |
| CaCl$_2$ x 2 H$_2$O | 0.05 to 0.3 | g |
| KH$_2$PO$_4$ | 0.2 to 0.5 | g |
| Yeast extract | 1.0 to 6.0 | g |
| Meat extract | 2.0 to 10.0 | g |
| Corn steep liquor | 1.0 to 5.0 | g |
| Peptone | 5.0 to 10 | g |
| Trace elements stock solution | 0.5 to 1.0 | ml |
| Resazurin, Na-salt | 0.25 | mg |
| L-cysteine | 0.5 | g |
| Distilled water | 1000 | ml |

All ingredients except for unmodified starch and L-cysteine were added and dissolved (except for CaCO$_3$) in deionized water and added into 2 L fermentation vessels with stirrers and pH and temperature control (company BBI-Biotech, Berlin). The pH-value should be between 6.8 and 7.0.

After autoclaving at 121 degree centigrade for 20 min and cooling down to room temperature (25 to 30 degrees centigrade) 50 g/L of unmodified pure potato starch (brand name Kuchenmeister, company Frießinger Mühle, Bad Wimpfen), was added and the medium was flushed with nitrogen gas (purity 99.999%) for 20 min at room temperature to remove excess oxygen before L-cysteine, which was dissolved as a stock solution in deionized water (100 g/L), and which had been filtered into a nitrogen containing serum flasks, was added to the medium. Then the fermentation was started by addition of the seed culture. Fermentation batch experiment was carried out in duplicate.

Then the temperature was increased from room temperature to 62 to 75 degree centigrade and the fermentation temperature during the process was regulated between these temperature ranges. PH-value was regulated from 5.8 to 7.2 after 18 h after the fermentation process had started by a solution of Ca(OH)$_2$ and NH$_4$OH. Samples were taken and L-lactic acid concentrations were by determined by Lactate biosensor as described in example 8. The results are presented in Table 8.

TABLE 8

L-lactic acid concentrations (average of two fermentations and deviation from average from unmodified starch (pure potato starch) by BluConL60 at different cultivation times.

| Cultivation time [h] | L-lactic acid [g/l] |
|---|---|
| 0.1 | 0.2 ± 0.1 |
| 19 | 10.6 ± 0.4 |
| 25 | 30.5 ± 0.2 |

The results of the fermentation samples show that BluConL60 produces L-lactic acid from unmodified starch.

LIST OF ADDITIONAL REFERENCES

Rainey F A, Donnison A M, Janssen P H, Saul D, Rodrigo A, Bergquist P L, Daniel R M, Stackebrandt E, Morgan H W. (1994) Description of *Caldicellulosiruptor saccharolyticus* gen. nov., sp. nov: an obligately anaerobic, extremely thermophilic, cellulolytic bacterium. FEMS Microbiol Lett. 120:263-266.

Sissons C H, Sharrock K R, Daniel R M, Morgan H W. (1987) Isolation of cellulolytic anaerobic extreme thermophiles from New Zealand thermal sites. Appl Environ Microbiol. 53:832-838.

Donnison A M, Brockelsby C M, Morgan H W, Daniel R M. (1989) The degradation of lignocellulosics by extremely thermophilic microorganisms. Biotechnol Bioeng. 33:1495-1499.

Hungate R E. (1969) A roll tube method for cultivation of strict anaerobes. In: Methods in Microbiology Eds. Norris J R and Ribbons D W. pp 118-132. New York: Academic Press.

Chenna R, Sugawara H, Koike T, Lopez R, Gibson T J, Higgins D G, Thompson J D. (2003) Multiple sequence alignment with the Clustal series of programs. Nucleic Acids Res. 13:3497-3500.

Kumar S, Tamura K, Jakobsen I B, Nei M. (2001) MEGA2: molecular evolutionary genetics analysis software. Bioinformatics. 17:1244-1245.

What is claimed is:

1. A method for converting lignocellulosic biomass and/or starch containing biomass to a carboxylic acid comprising the step of contacting the lignocellulosic biomass and/or the starch containing biomass with a microbial culture for a period of time at an initial temperature and an initial pH, thereby producing an amount of a carboxylic acid; wherein the microbial culture comprises an extremely thermophilic bacteria strain of the genus *Caldicellulosiruptor*, wherein the strain is selected from the group consisting of *Caldicellulosiruptor* sp. BluConL70 having the DSMZ Accession number 33496, *Caldicellulosiruptor* sp. BluConL60 having the DSMZ Accession number 33252, *Caldicellulosiruptor* sp. BluCon085 having the DSMZ Accession number 33485 *Caldicellulosiruptor* sp. BluCon052 having the DSMZ Accession number 33470, *Caldicellulosiruptor* sp. BluCon006 having the DSMZ Accession number 33095, *Caldicellulosiruptor* sp. BluCon014 having the DSMZ Accession number 33096, and *Caldicellulosiruptor* sp. BluCon016 having the DSMZ Accession number 33097, microorganism derived therefrom, progenies or mutants thereof, wherein the mutants thereof retaining the properties of BluCon0L70, BluConL60, BluCon085, BluCon052, BluCon006, BluCon014 and/or BluCon016.

2. The method according to claim 1, wherein the lignocellulosic biomass is selected from the group consisting of grass, switch grass, cord grass, rye grass, reed canary grass, mixed prairie grass, miscanthus, sugarcane bagasse, sugarcane straw, agricultural wastes, rice straw, rice hulls, barley straw, corn cobs, cereal straw, wheat straw, canola straw, oat straw, oat hulls, corn fiber, stover, soybean stover, corn stover, forestry wastes, recycled wood pulp fiber, paper sludge, sawdust, hardwood, softwood, pressmud from sugar beet, cotton stalk, banana leaves, and lignocellulosic biomass obtained through processing of food plants.

3. The method according to claim 1, wherein said lignocellulosic biomass is selected from the group consisting of corn stover, sugarcane bagasse, cotton stalks, and switchgrass.

4. The method according to claim 1, wherein said lignocellulosic biomass is a grass or perennial grass.

5. The method according to claim 1, wherein the starch containing biomass is selected from the group consisting of corn (maize), wheat, pea, barley, cassava, sorghum, rye, potato, or any combination thereof.

6. The method according to claim 5, further comprising the following pretreatment steps:

steaming and/or mechanically comminuting the lignocellulosic biomass and/or the starch-containing biomass, followed by exposure to sulfurous acid or its anhydride under heat with a sudden release of pressure,
milling, and
digestion with cellulose- and hemicellulose-degrading enzymes.

7. The method according to claim 6, wherein the carboxylic acid is lactic acid and/or salts or esters thereof.

8. A lactic acid production procedure, comprising:
a) converting starch and/or starch-containing material to lactic acid by a microorganism in a bioreactor as part of a consolidated bioprocessing system, wherein the microorganism is selected from the group consisting of *Caldicellulosiruptor* sp. BluConL70 having the DSMZ Accession number 33496, *Caldicellulosiruptor* sp. BluConL60 having the DSMZ Accession number 33252, *Caldicellulosiruptor* sp. BluCon085 having the DSMZ Accession number 33485, *Caldicellulosiruptor* sp. BluCon052 having the DSMZ Accession number 33470, *Caldicellulosiruptor* sp. BluCon006 having the DSMZ Accession number 33095, *Caldicellulosiruptor* sp. BluCon014 having the DSMZ Accession number 33096, and *Caldicellulosiruptor* sp. BluCon016 having the DSMZ Accession number 33097, microorganism derived therefrom, progenies or mutants thereof, wherein the mutants thereof retaining the properties of BluCon0L70, BluConL60, BluCon085, BluCon052, BluCon006, BluCon014 and/or BluCon016, wherein converting occurs;
b) separating lactic acid from the fermentation medium; and
c) purifying the lactic acid.

9. The lactic acid production procedure according to claim 8, wherein no amylolytic enzymes are added in step a).

10. The lactic acid production procedure according to claim 9, wherein the starch and/or starch-containing material is not heat treated before step a).

11. The lactic acid production procedure according to claim 8, wherein the bioreactor is a bioreactor with a stirrer, a bioreactor with different supports, a tower bioreactor, a horizontal tubular bioreactor, or other types of bioreactors.

12. The lactic acid production procedure according to claim 8, wherein the starch and/or starch-containing material is converted to lactic acid in 10 hours to 300 hours.

13. The lactic acid production procedure according to claim 8, wherein the starch and/or starch-containing material is converted to lactic acid in 40 hours to 300 hours.

14. The lactic acid production procedure according to claim 8, wherein the starch and/or starch-containing material is converted to lactic acid at a temperature between 55° C. and 80° C.

15. The lactic acid production procedure according to claim 8, wherein the starch and/or starch-containing material is converted to lactic acid at a pH between 5 and 9.

16. The lactic acid production procedure according to claim 8, wherein the starch-containing material comprises starch-containing plant material.

17. The lactic acid production procedure according to claim 8, wherein the starch containing material is selected from the group consisting of corn (maize), wheat, pea, barley, cassava, sorghum, rye, potato, and any combination thereof.

18. The lactic acid production procedure according to claim 8, wherein the starch and/or starch-containing material is subjected to mechanical pretreatment, thermochemical pretreatment, and/or biochemical pretreatment.

19. The lactic acid production procedure according to claim 18, wherein the starch and/or starch-containing material is pretreated with steam.

* * * * *

SEQUENCE LISTING

```
<160> NUMBER OF SEQ ID NOS: 8

<210> SEQ ID NO 1
<211> LENGTH: 1459
<212> TYPE: DNA
<213> ORGANISM: Caldicellulosiruptor spec.
<220> FEATURE:
<221> NAME/KEY: misc_feature
<222> LOCATION: (210)..(210)
<223> OTHER INFORMATION: n is a, c, g, or t
<220> FEATURE:
<221> NAME/KEY: misc_feature
<222> LOCATION: (220)..(221)
<223> OTHER INFORMATION: n is a, c, g, or t
<220> FEATURE:
<221> NAME/KEY: misc_feature
<222> LOCATION: (778)..(778)
<223> OTHER INFORMATION: n is a, c, g, or t

<400> SEQUENCE: 1
gcatgcagtc gagcggagat ggtggttgaa ggtgatgagc tggaggctgc catcttagcg      60
gcggacgggt gagtaacacg tgagcaacct accccagca cggggataac agctcgaaag      120
```
ggctgctaat acccgatggg accacgtcat cgcatggtga tgtggtgaaa gggctgggga    180
tgggctcgcg gcccatcagc tagttggtgn ggtaacggcn naccaaggcg acgacgggta    240
gccggcctga gagggtgtac ggccacagtg ggactgagac acggcccaca ctcctacggg    300
aggcagcagc ggggaatctt gcgcaatggg cggaagcctg acgcagcgac gccgcgtgag    360
ggaagaagcc cttcggggtg taaacctctt tggacgggga gaagtaggag atagtacccg    420
tttaaaaagc cacggctaac tacgtgccag cagccgcggt aatacgtagg tggcgagcgt    480
tgtccggaat tactgggcgt aaagggtgcg taggcggcta tgcgagttaa gcgtgaaagc    540
cttaggctca acctaaggat tgcgcttaat actgcatagc ttgagtgcgg gagaggacgg    600
cggaattccc ggtgtagcgg tgaaatgcgt agatatcggg aggaacacca gtggcgaagg    660
cggccgtctg gaccgtaact gacgctgagg cacgaaagcg tggggagcga acaggattag    720
ataccctggt agtccacgct gtaaacgatg gatgctaggt gtgggggaga aggactcntc    780
cgtgccgtag ttaacacaat aagcatcccg cctggggagt acggccgcaa ggttgaaact    840
caaaggaatt gacgggggcc cgcacaagcg gtggagcatg tggtttaatt cgaagcaacg    900
cgaagaacct taccagggct tgacatgccg gggacctgcc cgaaagggtg gggtgcctgt    960
tcgatgagag caggagcccg acacaggtg gtgcatggtt gtcgtcagct cgtgtcgtga    1020
gatgttgggt taagtcccgc aacgagcgca acccctgccc ttagttgcca gcgcgtaatg    1080
gtgggcactc taaggggact gccgtcgatg aggcggagga aggtggggat gacgtcaaat    1140
catcatgccc cttatgccct gggctacaca cgtgctacaa tgggtgctac agagggcgtg    1200
cgaaggcgcg agccggagcg aatcccaaaa aagcacccccc agttcggatt gcaggctgca    1260
actcgcctgc atgaagtcgg aatcgctagt aatcgcggat cagcatgccg cggtgaatac    1320
gttcccgggc cttgtacaca ccgcccgtca caccatgaga gtcagcaaca cctgaagaca    1380
caggttaagc tgtgttgaag gtggggctga tgattggggt gaagtcgtaa caaggtagcc    1440
gtacgggaac gtgcggctg                                                 1459

<210> SEQ ID NO 2
<211> LENGTH: 1460
<212> TYPE: DNA
<213> ORGANISM: Caldicellulosiruptor spec.
<220> FEATURE:
<221> NAME/KEY: misc_feature
<222> LOCATION: (212)..(212)
<223> OTHER INFORMATION: n is a, c, g, or t
<220> FEATURE:
<221> NAME/KEY: misc_feature
<222> LOCATION: (222)..(223)
<223> OTHER INFORMATION: n is a, c, g, or t
<220> FEATURE:
<221> NAME/KEY: misc_feature
<222> LOCATION: (780)..(780)
<223> OTHER INFORMATION: n is a, c, g, or t

<400> SEQUENCE: 2
acgcatgcag tcgagcggag atggtggttg aaggtgatga gctggaggct gccatcttag    60
cggcggacgg gtgagtaaca cgtgagcaac ctaccccag cacggggata acagctcgaa    120
agggctgcta atacccgatg ggaccacgtc atcgcatggt gatgtggtga aagggctggg    180
gatgggctcg cggcccatca gctagttggt gnggtaacgg cnnaccaagg cgacgacggg    240
tagccggcct gagagggtgt acggccacag tgggactgag acacggccca cactcctacg    300
ggaggcagca gcggggaatc ttgcgcaatg ggcggaagcc tgacgcagcg acgccgcgtg    360

```
agggaagaag cccttcgggg tgtaaacctc tttggacggg gagaagtagg agatagtacc    420
cgtttaaaaa gccacggcta actacgtgcc agcagccgcg gtaatacgta ggtggcgagc    480
gttgtccgga attactgggc gtaaaggtgt cgtaggcggc tatgcgagtt aagcgtgaaa    540
gccttaggct caacctaagg attgcgctta atactgcata gcttgagtgc gggagaggac    600
ggcggaattc ccggtgtagc ggtgaaatgc gtagatatcg gaggaacac cagtggcgaa     660
ggcggccgtc tggaccgtaa ctgacgctga ggcacgaaag cgtggggagc gaacaggatt    720
agataccctg gtagtccacg ctgtaaacga tggatgctag gtgtggggga aaggactcn     780
tccgtgccgt agttaacaca ataagcatcc gcctgggga gtacggccgc aaggttgaaa     840
ctcaaaggaa ttgacggggg cccgcacaag cggtggagca tgtggtttaa ttcgaagcaa    900
cgcgaagaac cttaccaggg cttgacatgc cggggacctg cccgaaaggg tggggtgcct    960
gttcgatgag agcaggagcc cggacacagg tggtgcatgg ttgtcgtcag ctcgtgtcgt    1020
gagatgttgg gttaagtccc gcaacgagcg caacccctgc ccttagttgc cagcgcgtaa    1080
tggtgggcac tctaagggga ctgccgtcga tgaggcggag aaggtggggg atgacgtcaa    1140
atcatcatgc cccttatgcc ctgggctaca cacgtgctac aatgggtgct acagagggcg    1200
tgcgaaggcg cgagccggag cgaatcccaa aaaagcaccc ccagttcgga ttgcaggctg    1260
caactcgcct gcatgaagtc ggaatcgcta gtaatcgcgg atcagcatgc cgcggtgaat    1320
acgttcccgg gccttgtaca caccgcccgt cacaccatga gagtcagcaa cacctgaaga    1380
cacaggttaa gctgtgttga aggtggggct gatgattggg gtgaagtcgt aacaaggtag    1440
ccgtacggga acgtgcggct                                                 1460

<210> SEQ ID NO 3
<211> LENGTH: 1459
<212> TYPE: DNA
<213> ORGANISM: Caldicellulosiruptor spec.
<220> FEATURE:
<221> NAME/KEY: misc_feature
<222> LOCATION: (211)..(211)
<223> OTHER INFORMATION: n is a, c, g, or t
<220> FEATURE:
<221> NAME/KEY: misc_feature
<222> LOCATION: (221)..(222)
<223> OTHER INFORMATION: n is a, c, g, or t
<220> FEATURE:
<221> NAME/KEY: misc_feature
<222> LOCATION: (779)..(779)
<223> OTHER INFORMATION: n is a, c, g, or t

<400> SEQUENCE: 3
cgcatgcagt cgagcggaga tggtggttga aggtgatgag ctggaggctg ccatcttagc     60
ggcggacggg tgagtaacac gtgagcaacc tacccccagc acggggataa cagctcgaaa    120
gggctgctaa tacccgatgg gaccacgtca tcgcatggta atgtggtgaa agggctgggg    180
atgggctcgc ggcccatcag ctagttggtg nggtaacggc nnaccaaggc gacgacgggt    240
agccggcctg agagggtgta cggccacagt gggactgaga cacggcccac actcctacgg    300
gaggcagcag cggggaatct tgcgcaatgg gcggaagcct gacgcagcga cgccgcgtga    360
gggaagaagc ccttcgggt gtaaacctct ttggacggg agaagtagga gatagtaccc      420
gtttaaaaag ccacggctaa ctacgtgcca gcagccgcgg taatacgtag gtggcgagcg    480
ttgtccggaa ttactgggcg taaagggtgc gtaggcggct atgcgagtta agcgtgaaag    540
ccttaggctc aacctaagga ttgcgcttaa tactgcatag cttgagtgcg ggagaggacg    600
gcggaattcc cggtgtagcg gtgaaatgcg tagatatcgg aggaacacc agtggcgaag     660
```

```
gcggccgtct ggaccgtaac tgacgctgag gcacgaaagc gtggggagcg aacaggatta      720
gataccctgg tagtccacgc tgtaaacgat ggatgctagg tgtgggggag aaggactcnt      780
ccgtgccgta gttaacacaa taagcatccc gcctggggag tacggccgca aggttgaaac      840
tcaaaggaat tgacggggc  ccgcacaagc ggtggagcat gtggtttaat tcgaagcaac      900
gcgaagaacc ttaccagggc ttgacatgcc ggggacctgc ccgaaagggt ggggtgcctg      960
ttcgatgaga gcaggagccc ggacacaggt ggtgcatggt tgtcgtcagc tcgtgtcgtg     1020
agatgttggg ttaagtcccg caacgagcgc aaccoctgcc cttagttgcc agcgcgtaat     1080
ggtgggcact ctaaggggac tgccgtcgat gaggcggagg aaggtgggga tgacgtcaaa     1140
tcatcatgcc ccttatgccc tgggctacac acgtgctaca atgggtgcta cagagggcgt     1200
gcgaaggcgc gagccggagc gaatcccaaa aaagcacccc cagttcggat tgcaggctgc     1260
aactcgcctg catgaagtcg gaatcgctag taatcgcgga tcagcatgcc gcggtgaata     1320
cgttcccggg ccttgtacac accgcccgtc acaccatgag agtcagcaac acctgaagac     1380
acaggttaag ctgtgttgaa ggtggggctg atgattgggg tgaagtcgta acaaggtagc     1440
cgtacgggaa cgtgcggct                                                  1459

<210> SEQ ID NO 4
<211> LENGTH: 1459
<212> TYPE: DNA
<213> ORGANISM: Caldicellosiruptor spec.
<220> FEATURE:
<221> NAME/KEY: misc_feature
<222> LOCATION: (210)..(210)
<223> OTHER INFORMATION: n is a, c, g, or t
<220> FEATURE:
<221> NAME/KEY: misc_feature
<222> LOCATION: (220)..(221)
<223> OTHER INFORMATION: n is a, c, g, or t
<220> FEATURE:
<221> NAME/KEY: misc_feature
<222> LOCATION: (778)..(778)
<223> OTHER INFORMATION: n is a, c, g, or t

<400> SEQUENCE: 4
gcatgcagtc gagcggagat ggtggttgaa ggtgatgagc tggaggctgc catcttagcg       60
gcggacgggt gagtaacacg tgagcaacct accoccagca cggggataac agctcgaaag      120
ggctgctaat acccgatggg accacgtcat cgcatggtga tgtggtgaaa gggctgggga      180
tgggctcgcg gcccatcagc tagttggtgn ggtaacggcn naccaaggcg acgacgggta      240
gccggcctga gagggtgtac ggccacagtg ggactgagac acggcccaca ctcctacggg      300
aggcagcagc ggggaatctt gcgcaatggg cggaagcctg acgcagcgac gccgcgtgag      360
ggaagaagcc cttcggggtg taaacctctt tggacgggga gaagtaggag atagtacccg      420
tttaaaaagc cacggctaac tacgtgccag cagccgcggt aatacgtagg tggcgagcgt      480
tgtccggaat tactgggcgt aaagggtgcg taggcggcta tgcgagttaa gcgtgaaagc      540
cttaggctca acctaaggat tgcgcttaat actgcatagc ttgagtgcgg gagaggacgg      600
cggaattccc ggtgtagcgg tgaaatgcgt agatatcggg aggaacacca gtggcgaagg      660
cggccgtctg gaccgtaact gacgctgagg cacgaaagcg tggggagcga acaggattag      720 atacccctggt agtccacgct gtaaacgatg gatgctaggt gtgggggaga aggactcntc      780
cgtgccgtag ttaacacaat aagcatcccg cctggggagt acggccgcaa ggttgaaact      840
caaaggaatt gacggggccc cgcacaagcg gtggagcatg tggtttaatt cgaagcaacg      900
```

| | |
|---|---|
| cgaagaacct taccagggct tgacatgccg gggacctgcc cgaaagggtg gggtgcctgt | 960 |
| tcgatgagag caggagcccg gacacaggtg gtgcatggtt gtcgtcagct cgtgtcgtga | 1020 |
| gatgttgggt taagtcccgc aacgagcgca acccctgccc ttagttgcca gcgcgtaatg | 1080 |
| gtgggcactc taaggggact gccgtcgatg aggcggagga aggtggggat gacgtcaaat | 1140 |
| catcatgccc cttatgccct gggctacaca cgtgctacaa tgggtgctac agagggcgtg | 1200 |
| cgaaggcgcg agccggagcg aatcccaaaa aagcacccc agttcggatt gcaggctgca | 1260 |
| actcgcctgc atgaagtcgg aatcgctagt aatcgcggat cagcatgccg cggtgaatac | 1320 |
| gttcccgggc cttgtacaca ccgcccgtca caccatgaga gtcagcaaca cctgaagaca | 1380 |
| caggttaagc tgtgttgaag gtggggctga tgattggggt gaagtcgtaa caaggtagcc | 1440 |
| gtacgggaac gtgcggctg | 1459 |

```
<210> SEQ ID NO 5
<211> LENGTH: 1497
<212> TYPE: DNA
<213> ORGANISM: Caldicellulosiruptor spec.
<220> FEATURE:
<221> NAME/KEY: misc_feature
<222> LOCATION: (173)..(180)
<223> OTHER INFORMATION: n is a, c, g, or t
<220> FEATURE:
<221> NAME/KEY: misc_feature
<222> LOCATION: (183)..(184)
<223> OTHER INFORMATION: n is a, c, g, or t
<220> FEATURE:
<221> NAME/KEY: misc_feature
<222> LOCATION: (186)..(192)
<223> OTHER INFORMATION: n is a, c, g, or t
<220> FEATURE:
<221> NAME/KEY: misc_feature
<222> LOCATION: (231)..(231)
<223> OTHER INFORMATION: n is a, c, g, or t
<220> FEATURE:
<221> NAME/KEY: misc_feature
<222> LOCATION: (242)..(242)
<223> OTHER INFORMATION: n is a, c, g, or t
<220> FEATURE:
<221> NAME/KEY: misc_feature
<222> LOCATION: (799)..(799)
<223> OTHER INFORMATION: n is a, c, g, or t
```

<400> SEQUENCE: 5

| | |
|---|---|
| cgcatgcaag tcgagcggag atggtggttg aaggtgatga gctggaggct gccatcttag | 60 |
| cggcggacgg gtgagtaaca cgtgagcaac ctaccccag cacgggata acagctcgaa | 120 |
| agggctgcta atacccgatg ggaccacgtc atcgcatggt gatgtggtga annnnnnnn | 180 |
| ggnngnnnnn nnggctgggg atgggctcgc ggcccatcag ctagttggtg nggtaacggc | 240 |
| tnaccaaggc gacgacgggt agccggcctg agagggtgta cggccacagt gggactgaga | 300 |
| cacggcccac actcctacgg gaggcagcag cggggaatct tgcgcaatgg gcggaagcct | 360 |
| gacgcagcga cgccgcgtga gggaagaagc ccttcggggt gtaaacctct ttggacgggg | 420 |
| agaagtagga gatagtaccc gtttaaaaag ccacggctaa ctacgtgcca gcagccgcgg | 480 |
| taatacgtag gtggcgagcg ttgtccggaa ttactgggcg taaagggtgc gtaggcggct | 540 |
| atgcgagtta agcgtgaaag ccttaggctc aacctaagga ttgcgcttaa tactgcatag | 600 |
| cttgagtgcg ggagaggacg gcggaattcc cggtgtagcg gtgaaatgcg tagatatcgg | 660 |
| gaggaacacc agtggcgaag gcggccgtct ggaccgtaac tgacgctgag gcacgaaagc | 720 |
| gtggggagcg aacaggatta gataccctgg tagtccacgc tgtaaacgat ggatgctagg | 780 |
| tgtgggggag aaggactcnt ccgtgccgta gttaacacaa taagcatccc gcctggggag | 840 |

```
tacggccgca aggttgaaac tcaaaggaat tgacggggc  ccgcacaagc ggtggagcat      900
gtggtttaat tcgaagcaac gcgaagaacc ttaccagggc ttgacatgcc ggggacctgc      960
ccgaaagggt ggggtgcctg ttcgatgaga gcaggagccc ggacacaggt ggtgcatggt     1020
tgtcgtcagc tcgtgtcgtg agatgttggg ttaagtcccg caacgagcgc aaccctgcc      1080 cttagttgcc agcgcgtaat ggtgggcact ctaaggggac tgccgtcgat gaggcggagg     1140
aaggtgggga tgacgtcaaa tcatcatgcc cctatgccc  tgggctacac acgtgctaca     1200
atgggtgcta cagagggcgt gcgaaggcgc gagccggagc gaatcccaaa aaagcacccc     1260
cagttcggat tgcaggctgc aactcgcctg catgaagtcg gaatcgctag taatcgcgga     1320
tcagcatgcc gcggtgaata cgttcccggg ccttgtacac accgcccgtc acaccatgag     1380
agtcagcaac acctgaagac acaggttaag ctgtgttgaa ggtggggctg atgattgggg     1440
tgaagtcgta acaaggtagc cgtacgggaa cgtgcggctg gatcaccctc ctttcta       1497
```

<210> SEQ ID NO 6
<211> LENGTH: 1497
<212> TYPE: DNA
<213> ORGANISM: Caldicellulosiruptor spec.
<220> FEATURE:
<221> NAME/KEY: misc_feature
<222> LOCATION: (173)..(180)
<223> OTHER INFORMATION: n is a, c, g, or t
<220> FEATURE:
<221> NAME/KEY: misc_feature
<222> LOCATION: (183)..(184)
<223> OTHER INFORMATION: n is a, c, g, or t
<220> FEATURE:
<221> NAME/KEY: misc_feature
<222> LOCATION: (186)..(192)
<223> OTHER INFORMATION: n is a, c, g, or t
<220> FEATURE:
<221> NAME/KEY: misc_feature
<222> LOCATION: (231)..(231)
<223> OTHER INFORMATION: n is a, c, g, or t
<220> FEATURE:
<221> NAME/KEY: misc_feature
<222> LOCATION: (242)..(242)
<223> OTHER INFORMATION: n is a, c, g, or t
<220> FEATURE:
<221> NAME/KEY: misc_feature
<222> LOCATION: (799)..(799)
<223> OTHER INFORMATION: n is a, c, g, or t

<400> SEQUENCE: 6

```
cgcatgcaag tcgagcggag atggtggttg aaggtgatga gctggaggct gccatcttag       60
cggcggacgg gtgagtaaca cgtgagcaac ctaccccag  cacggggata acagctcgaa      120
agggctgcta atacccgatg ggaccacgtc atcgcatggt gatgtggtga aannnnnnnn      180
ggnngnnnnn nnggctgggg atgggctcgc ggcccatcag ctagttggtg nggtaacggc      240
tnaccaaggc gacgacgggt agccggcctg agagggtgta cggccacagt gggactgaga      300
cacggcccac actcctacgg gaggcagcag cgggaatct  tgcgcaatgg gcggaagcct      360
gacgcagcga cgccgcgtga gggaagaagc ccttcgggt  gtaaacctct ttggacgggg      420
agaagtagga gatagtaccc gtttaaaaag ccacggctaa ctacgtgcca gcagccgcgg      480
taatacgtag gtgcgagcg  ttgtccggaa ttactgggcg taaagggtgc gtaggcggct      540
atgcgagtta agcgtgaaag ccttaggctc aacctaagga ttgcgcttaa tactgcatag      600
cttgagtgcg ggagaggacg gcggaattcc cggtgtagcg gtgaaatgcg tagatatcgg      660
gaggaacacc agtggcgaag gcggccgtct ggaccgtaac tgacgctgag gcacgaaagc      720
```

| | |
|---|---:|
| gtggggagcg aacaggatta gatacccctgg tagtccacgc tgtaaacgat ggatgctagg | 780 |
| tgtgggggag aaggactcnt ccgtgccgta gttaacacaa taagcatccc gcctggggag | 840 |
| tacggccgca aggttgaaac tcaaaggaat tgacggggggc ccgcacaagc ggtggagcat | 900 |
| gtggtttaat tcgaagcaac gcgaagaacc ttaccagggc ttgacatgcc ggggacctgc | 960 |
| ccgaaagggt ggggtgcctg ttcgatgaga gcaggagccc ggacacaggt ggtgcatggt | 1020 |
| tgtcgtcagc tcgtgtcgtg agatgttggg ttaagtcccg caacgagcgc aaccccctgcc | 1080 |
| cttagttgcc agcgcgtaat ggtgggcact ctaagggac tgccgtcgat gaggcggagg | 1140 |
| aaggtgggga tgacgtcaaa tcatcatgcc ccttatgccc tgggctacac acgtgctaca | 1200 |
| atgggtgcta cagagggcgt gcgaaggcgc gagccggagc gaatcccaaa aaagcacccc | 1260 |
| cagttcggat tgcaggctgc aactcgcctg catgaagtcg gaatcgctag taatcgcgga | 1320 |
| tcagcatgcc gcggtgaata cgttcccggg ccttgtacac accgcccgtc acaccatgag | 1380 |
| agtcagcaac acctgaagac acaggttaag ctgtgttgaa ggtggggctg atgattgggg | 1440 |
| tgaagtcgta acaaggtagc cgtacgggaa cgtgcggctg atcaccctc ctttcta | 1497 |

<210> SEQ ID NO 7
<211> LENGTH: 1497
<212> TYPE: DNA
<213> ORGANISM: Caldicellulosiruptor spec.
<220> FEATURE:
<221> NAME/KEY: misc_feature
<222> LOCATION: (173)..(180)
<223> OTHER INFORMATION: n is a, c, g, or t
<220> FEATURE:
<221> NAME/KEY: misc_feature
<222> LOCATION: (183)..(184)
<223> OTHER INFORMATION: n is a, c, g, or t
<220> FEATURE:
<221> NAME/KEY: misc_feature
<222> LOCATION: (186)..(192)
<223> OTHER INFORMATION: n is a, c, g, or t
<220> FEATURE:
<221> NAME/KEY: misc_feature
<222> LOCATION: (231)..(231)
<223> OTHER INFORMATION: n is a, c, g, or t
<220> FEATURE:
<221> NAME/KEY: misc_feature
<222> LOCATION: (242)..(242)
<223> OTHER INFORMATION: n is a, c, g, or t
<220> FEATURE:
<221> NAME/KEY: misc_feature
<222> LOCATION: (799)..(799)
<223> OTHER INFORMATION: n is a, c, g, or t

<400> SEQUENCE: 7

| | |
|---|---:|
| cgcatgcaag tcgagcggag atggtggttg aaggtgatga gctggaggct gccatcttag | 60 |
| cggcggacgg gtgagtaaca cgtgagcaac ctaccccccag cacggggata acagctcgaa | 120 |
| agggctgcta ataccccgatg ggaccacgtc atcgcatggt gatgtggtga aannnnnnnn | 180 |
| ggnngnnnnn nnggctgggg atgggctcgc ggcccatcag ctagttggtg nggtaacggc | 240 |
| tnaccaaggc gacgacgggt agccggcctg agagggtgta cggccacagt gggactgaga | 300 |
| cacggcccac actcctacgg gaggcagcag cggggaatct tgcgcaatgg gcggaagcct | 360 |
| gacgcagcga cgccgcgtga gggaagaagc ccttcggggt gtaaacctct ttggacgggg | 420 |
| agaagtagga gatagtaccc gtttaaaaag ccacggctaa ctacgtgcca gcagccgcgg | 480 |
| taatacgtag gtggcgagcg ttgtccggaa ttactgggcg taaagggtgc gtaggcggct | 540 |
| atgcgagtta agcgtgaaag ccttaggctc aacctaagga ttgcgcttaa tactgcatag | 600 |
| cttgagtgcg ggagaggacg gcggaattcc cggtgtagcg gtgaaatgcg tagatatcgg | 660 |

-continued

```
gaggaacacc agtggcgaag gcggccgtct ggaccgtaac tgacgctgag gcacgaaagc    720
gtggggagcg aacaggatta gataccctgg tagtccacgc tgtaaacgat ggatgctagg    780
tgtgggggag aaggactcnt ccgtgccgta gttaacacaa taagcatccc gcctggggag    840 tacgccgca aggttgaaac tcaaaggaat tgacgggggg ccgcacaagc ggtggagcat    900
gtggtttaat tcgaagcaac gcgaagaacc ttaccagggc ttgacatgcc ggggacctgc    960
ccgaaagggt ggggtgcctg ttcgatgaga gcaggagccc ggacacaggt ggtgcatggt   1020
tgtcgtcagc tcgtgtcgtg agatgttggg ttaagtcccg caacgagcgc aaccccctgcc  1080 cttagttgcc agcgcgtaat ggtgggcact ctaagggac tgccgtcgat gaggcggagg    1140
aaggtgggga tgacgtcaaa tcatcatgcc ccttatgccc tgggctacac acgtgctaca   1200
atgggtgcta cagagggcgt gcgaaggcgc gagccggagc gaatcccaaa aaagcacccc   1260
cagttcggat tgcaggctgc aactcgcctg catgaagtcg gaatcgctag taatcgcgga   1320
tcagcatgcc gcggtgaata cgttcccggg ccttgtacac accgcccgtc accatgag    1380 agtcagcaac acctgaagac acaggttaag ctgtgttgaa ggtggggctg atgattgggg   1440
tgaagtcgta acaaggtagc cgtacgggaa cgtgcggctg atcaccctc ctttcta       1497
```

<210> SEQ ID NO 8
<211> LENGTH: 1473
<212> TYPE: DNA
<213> ORGANISM: Caldicellulosiruptor spec.
<220> FEATURE:
<221> NAME/KEY: misc_feature
<222> LOCATION: (209)..(209)
<223> OTHER INFORMATION: n is a, c, g, or t
<220> FEATURE:
<221> NAME/KEY: misc_feature
<222> LOCATION: (220)..(220)
<223> OTHER INFORMATION: n is a, c, g, or t
<220> FEATURE:
<221> NAME/KEY: misc_feature
<222> LOCATION: (777)..(777)
<223> OTHER INFORMATION: n is a, c, g, or t

<400> SEQUENCE: 8

```
catgcagtcg agcggagatg gtggttgaag gtgatgagct ggaggctgcc atcttagcgg     60
cggacgggtg agtaacacgt gagcaaccta cccccagcac ggggataaca gctcgaaagg    120
gctgctaata cccgatggga ccacgtcatc gcatggtgat gtggtgaaag gctggggat    180 gggctcgcgg cccatcagct agttggtgng gtaacggctn accaaggcga cgacgggtag    240
ccggcctgag agggtgtacg gccacagtgg gactgagaca cggcccacac tcctacggga    300
ggcagcagcg gggaatcttg cgcaatgggc ggaagcctga cgcagcgacg ccgcgtgagg    360
gaagaagccc ttcgggtgt aaacctcttt ggacggggag aagtaggaga tagtacccgt    420
ttaaaaagcc acggctaact acgtgccagc agccgcggta atacgtaggt ggcgagcgtt    480
gtccggaatt actgggcgta aagggtgcgt aggcggctat gcgagttaag cgtgaaagcc    540
ttaggctcaa cctaaggatt gcgcttaata ctgcatagct tgagtgcggg agaggacggc    600
ggaattcccg gtgtagcggt gaaatgcgta gatatcggga ggaacaccag tggcgaaggc    660
ggccgtctgg accgtaactg acgctgaggc acgaaagcgt ggggagcgaa caggattaga    720
taccctggta gtccacgctg taaacgatgg atgctaggtg tgggggagaa ggactcntcc    780
gtgccgtagt taacacaata agcatcccgc ctggggagta cggccgcaag gttgaaactc    840
aaaggaattg acggggccc gcacaagcgg tggagcatgt ggtttaattc gaagcaacgc    900
```

```
gaagaacctt accagggctt gacatgccgg ggacctgccc gaaagggtgg ggtgcctgtt      960
cgatgagagc aggagcccgg acacaggtgg tgcatggttg tcgtcagctc gtgtcgtgag     1020
atgttgggtt aagtcccgca acgagcgcaa cccctgccct tagttgccag cgcgtaatgg     1080
tgggcactct aaggggactg ccgtcgatga ggcggaggaa ggtggggatg acgtcaaatc     1140
atcatgcccc ttatgccctg ggctacacac gtgctacaat gggtgctaca gagggcgtgc     1200
gaaggcgcga gccggagcga atcccaaaaa agcaccccca gttcggattg caggctgcaa     1260
ctcgcctgca tgaagtcgga atcgctagta atcgcggatc agcatgccgc ggtgaatacg     1320
ttcccgggcc ttgtacacac cgcccgtcac accatgagag tcagcaacac ctgaagacac     1380
aggttaagct gtgttgaagg tgggggctgat gattggggtg aagtcgtaac aaggtagccg     1440
tacgggaacg tgcggctgga tcacctcctt tct                                  1473
```